US010464979B2

(12) United States Patent
Mohammadi et al.

(10) Patent No.: US 10,464,979 B2
(45) Date of Patent: Nov. 5, 2019

(54) FGF23 C-TAIL FUSION PROTEINS

(71) Applicants: NEW YORK UNIVERSITY, New York, NY (US); PFIZER INC., New York, NY (US)

(72) Inventors: Moosa Mohammadi, Scarsdale, NY (US); Regina Goetz, New York, NY (US); Jeanne Sue Magram, Croton-on-Hudson, NY (US); Kristen Leigh Johnson, New York, NY (US)

(73) Assignees: New York University, New York, NY (US); Pfizer Inc., New York, NY (US)

( * ) Notice: Subject to any disclaimer, the term of this patent is extended or adjusted under 35 U.S.C. 154(b) by 0 days.

(21) Appl. No.: 15/300,048

(22) PCT Filed: Mar. 30, 2015

(86) PCT No.: PCT/US2015/023349
§ 371 (c)(1),
(2) Date: Sep. 28, 2016

(87) PCT Pub. No.: WO2015/149069
PCT Pub. Date: Oct. 1, 2015

(65) Prior Publication Data
US 2017/0226172 A1 Aug. 10, 2017

Related U.S. Application Data

(60) Provisional application No. 61/972,081, filed on Mar. 28, 2014.

(51) Int. Cl.
| *A61K 38/18* | (2006.01) |
|---|---|
| *A61K 39/395* | (2006.01) |
| *C07K 14/50* | (2006.01) |
| *C07K 16/46* | (2006.01) |
| *A61K 38/00* | (2006.01) |

(52) U.S. Cl.
CPC .......... *C07K 14/50* (2013.01); *A61K 38/1825* (2013.01); *A61K 38/00* (2013.01); *C07K 2319/30* (2013.01); *C07K 2319/35* (2013.01); *C07K 2319/75* (2013.01)

(58) Field of Classification Search
None
See application file for complete search history.

(56) References Cited

U.S. PATENT DOCUMENTS

| 5,624,821 A | 4/1997 | Winter et al. |
|---|---|---|
| 5,648,260 A | 7/1997 | Winter et al. |
| 7,223,563 B2 | 5/2007 | Econs et al. |
| 7,314,618 B2 | 1/2008 | Econs et al. |
| 7,745,406 B2 | 6/2010 | Econs et al. |
| 7,947,810 B2 | 5/2011 | Econs et al. |
| 8,889,426 B2 | 11/2014 | Mohammadi et al. |
| 8,889,621 B2 | 11/2014 | Mohammadi et al. |
| 9,272,017 B2 | 3/2016 | Mohammadi et al. |
| 9,464,126 B2 | 10/2016 | Mohammadi et al. |
| 9,474,785 B2 | 10/2016 | Mohammadi et al. |
| 9,475,856 B2 | 10/2016 | Mohammadi et al. |
| 9,550,820 B2 | 1/2017 | Mohammadi et al. |
| 9,657,075 B2 | 5/2017 | Mohammadi et al. |
| 9,907,830 B2 | 3/2018 | Mohammadi et al. |
| 9,926,355 B2 | 3/2018 | Mohammadi et al. |
| 9,926,356 B2 | 3/2018 | Mohammadi et al. |
| 2002/0082205 A1 | 6/2002 | Itoh et al. |
| 2003/0105302 A1 | 6/2003 | Itoh et al. |
| 2004/0043457 A1* | 3/2004 | Schumacher .......... A61K 38/47 435/69.7 |
| 2004/0097414 A1 | 5/2004 | Itoh et al. |
| 2006/0160181 A1 | 7/2006 | Luethy et al. |
| 2006/0281679 A1 | 12/2006 | Itoh et al. |
| 2009/0192087 A1 | 7/2009 | Glass et al. |
| 2010/0323954 A1 | 12/2010 | Li et al. |
| 2011/0104152 A1 | 5/2011 | Sonoda |

(Continued)

FOREIGN PATENT DOCUMENTS

| JP | H01502875 A | 10/1989 |
|---|---|---|
| JP | 2008-117661 | 7/2008 |

(Continued)

OTHER PUBLICATIONS

Isakova et al., "Fibroblast Growth Factor 23 and Adverse Clinical Outcomes in Chronic Kidney Disease," NIH Public Access, Author Manuscript (available May 1, 2013), published in final edited Form in Curr. Opin. Neprhol. Hypertens. 21(3):334-340 (2012).
Supplementary European Search Report in corresponding European Patent Application No. EP 15767912.7, 12 pages (Aug. 4, 2017).
Razzaque et al., "Therapeutic Potential of Klotho-FGF23 Fusion Polypeptides: W02009095372," Expert Opin. Ther. Pat. 20(7):981-5 (2010).
Czajkowsky et al., "Fc-Fusion Proteins: New Developments and Future Perspectives," EMBO Mol. Med. 4(10): 1015-1028 (2012).
Creative Biomart, Specification Sheet, "Recombinant Human Fibroblast Growth Factor 23, Fc Chimera," http://www.creativebiomart.net/pdf/FGF23-416H,FGF23,Fc Chimera.pdf, Rev 092708A (cited in European Search Report in EP15767912.7 as NPL reference XP055393212).

(Continued)

*Primary Examiner* — Christine J Saoud
(74) *Attorney, Agent, or Firm* — Pepper Hamilton LLP

(57) ABSTRACT

Disclosed herein are FGF23 c-tail fusion proteins, pharmaceutical compositions comprising the FGF23 c-tail fusion proteins, and methods of treatment using the FGF23 c-tail fusion proteins. This application discloses fusion proteins comprising a FGF-23 c-tail protein fused to a heterologous amino acid sequence, wherein said fusion protein modulates serum phosphate levels but does not substantially modulate serum 1, 25 VitD levels. In some embodiments, the FGF-23 c-tail protein is fused to the heterologous amino acid sequence via a linker. This invention also encompasses vectors comprising the nucleic acids disclosed herein, and a host cell comprising the vector or polynucleotides encoding the proteins of the invention.

14 Claims, 22 Drawing Sheets

Specification includes a Sequence Listing.

(56) References Cited

U.S. PATENT DOCUMENTS

| | | |
|---|---|---|
| 2011/0171218 A1 | 7/2011 | Seehra et al. |
| 2011/0190207 A1* | 8/2011 | Mohammadi ......... A61K 38/17 514/13.5 |
| 2012/0288886 A1 | 11/2012 | Mohammadi et al. |
| 2013/0172275 A1 | 7/2013 | Mohammadi et al. |
| 2013/0184211 A1 | 7/2013 | Mohammadi et al. |
| 2013/0331325 A1 | 12/2013 | Mohammadi et al. |
| 2017/0029480 A1 | 2/2017 | Mohammadi et al. |
| 2017/0096462 A1 | 4/2017 | Mohammadi et al. |
| 2017/0101449 A1 | 4/2017 | Mohammadi et al. |
| 2017/0355738 A1 | 12/2017 | Mohammadi et al. |
| 2018/0186849 A1 | 7/2018 | Mohammadi et al. |
| 2018/0186850 A1 | 7/2018 | Mohammadi et al. |

FOREIGN PATENT DOCUMENTS

| | | |
|---|---|---|
| JP | 2013-512674 A | 4/2013 |
| WO | 88/07089 A1 | 9/1988 |
| WO | WO 2001/066595 A2 | 9/2001 |
| WO | WO 2001/066596 A2 | 9/2001 |
| WO | 2006/031653 A2 | 3/2006 |
| WO | 2007/120766 A2 | 10/2007 |
| WO | 2009095372 A1 | 8/2009 |
| WO | 2009/133905 A1 | 11/2009 |
| WO | WO 2009/133905 A1 | 11/2009 |
| WO | 2011/068993 A1 | 6/2011 |
| WO | WO 2013/027191 A1 | 2/2013 |
| WO | 2013184958 A1 | 12/2013 |
| WO | WO 2015/149069 A1 | 10/2015 |

OTHER PUBLICATIONS

Creative Biomart, Specification Sheet, "Recombinant Mouse Fibroblast Growth Factor 23, Fc Chimera," http://www.creativebiomart.net/pdf/FGF23-417M,FGF23,Fc Chimera.pdf, Rev 092708A (cited in European Search Report in EP15767912.7 as NPL reference XP055393213).

Liu et al., "SUMO Fusion System Facilitates Soluble Expression and High Production of Bioactive Human Fibroblast Growth Factor 23 (FGF23)," Appl. Micro. Biotech. 96(1):103-111 (2012).

Aono et al., "Therapeutic Effects of Anti-FGF23 Antibodies in Hypophosphatemic Rickets/Osteomalacia," J. Bone Miner. Res. 24(11):1879-1888 (available online May 4, 2009).

Aono et al., "The Neutralization of FGF-23 Ameliorates Hypophosphatemia and Rickets in Hyp Mice," Abstract, Oral Presentation, No. 1056, 25th American Society for Bone and Mineral Research Meeting, Sep. 19-23, 2003, Minneapolis, Minnesota, J. Bone Miner. Res. 18 (Suppl. S1): S15 (2003).

Shimada et al., "Mutant FGF-23 Responsible for Autosomal Dominant Hypophosphatemic Rickets Is Resistant to Proteolytic Cleavage and Causes Hypophosphatemia in Vivo," Endocrinology 143(8):3179-82 (2002).

Shimada et al., "Neutralization of Intrinsic FGF-23 Action by Antibodies Reveals the Essential Role of FGF-23 in Physiological Phosphate and Vitamin D Metabolism," Abstract, Poster Presentation, Nos. SA414 and F414, 25th American Society for Bone and Mineral Research Meeting, Sep. 19-23, 2003, Minneapolis, Minnesota, J. Bone Miner. Res. 18 (Suppl. S1): S93, S164 (2003).

Wu et al., "C-terminal Tail of FGF19 Determines its Specificity Towards Klotho Co-receptors," J.Biol Chem. 283(48):33304-33309 (2008).

Yamazaki et al., "Anti-FGF23 Neutralizing Antibodies Show the Physiological Role and Structural Features of FGF23," J. Bone Miner. Res. 23(9):1509-1518 (available online Apr. 21, 2008).

Berndt et al., "Biological Activity of FGF-23 Fragments," Eur J Physiol 454:615-623 (2007).

Goetz et al., "Molecular Insights into the Klotho-Dependent, Endocrine Mode of Action of Fibroblast Growth Factor 19 Subfamily Members," Molecular and Cellular Biology 27(9):3417-3428 (2007).

Goetz et al., "Isolated C-Terminal tail of FGF23 Alleviates Hypophosphatemia by Inhibiting FGF23-FGFR-Klotho Complex Formation," PNAS 107(1):407-412 (2010).

Hu et al., "C-terminal Fragments of Fibroblast Growth Factor (FGF) 23 Inhibits Renal Phosphate (Pi) Excretion as an FGF23 Antagonist by Displacing FGF23 from its Receptor," Abstract SA-FC345, J. Am. Soc. Nephrol. 19:78A (2008).

Hu et al., "C-terminal Fragments of Fibroblast Growth Factor (FGF) 23 Inhibit Renal Phosphate Excretion as an FGF23 Antagonist by Displacing FGF23 from its Receptor," Oral Presentation at the 41st Annual Meeting of the American Society of Nephrology (Renal Week 2008) Philadelphia, PA, Nov. 4-9, 2008.

Shimada, "Possible Roles of Fibroblast Growth Factor 23 in Developing X-Linked Hypophosphatemia," Clin. Pediatr. Endocrinol. 14(Suppl. 23):33-37 (2005).

Kurosu et al., "Regulation of Fibroblast Growth Factor-23 Signaling by Klotho," J. Biol. Chem. 281(10):6120-6123 (2006).

Kurosu et al., "Tissue-Specific Expression of Betaklotho and Fibroblast Growth Factor (FGF) Receptor Isoforms Determines Metabolic Activity of FGF19 and FGF21," J. Biol. Chem. 282(37):26687-26695 (2007).

Micanovic et al., "Different Roles of N- and C-Termini in the Functional Activity of FGF21," J. Cell. Physiol. 219:227-234 (2009).

Kharitonenkov et al., "FGF-21/FGF-21 Receptor Interaction and Activation is Determined by BetaKlotho," J. Cell. Physiol. 215:1-7 (2008).

Beenken et al., "The FGF Family: Biology, Pathophysiology and Therapy," Nat Rev Drug Discov. 8(3):235-53 (Mar. 2009).

Perwad et al. "Fibroblast Growth Factor 23 Impairs Phosphorus and Vitamin D Metabolism in Vivo and Suppresses 25-Hydroxyvitamin D-1alpha-Hydroxylase Expression in Vitro," Am. J. Physiol. Renal Physiol. 293:F1577-F1583 (2007).

Razzaque, "The FGF23-Klotho Axis: Endocrine Regulation of Phosphate Homeostasis," Nat. Rev. Endocrinol. 5(11):611-19 (Nov. 2009).

Wu et al., "Separating Mitogenic and Metabolic Activities of Fibroblast Growth Factor 19 (FGF19)," Proc. Nat'l. Acad. Sci. USA 107(32):14158-14163 (Epub Jul. 26, 2010).

Faul et al., "FGF23 Induces Left Ventricular Hypertrophy," J Clin Invest 121(11):4393-4408 (2011).

Fliser et al., "Fibroblast Growth Factor 23 (FGF23) Predicts Progression of Chronic Kidney Disease: The Mild to Moderate Kidney Disease (MMKD) Study," J. Am. Soc. Nephrol. 18(9):2600-2608 (2007).

Gutierrez et al., "Fibroblast Growth Factor-23 Mitigates Hyperphosphatemia but Accentuates Calcitriol Deficiency in Chronic Kidney Disease," J. Am. Soc. Nephrol. 16(7):2205-2215 (2005).

Gutierrez et al., "Fibroblast Growth Factor 23 and Mortality Among Patients Undergoing Hemodialysis," N Engl. J. Med. 359(6):584-592 (2008).

Gutierrez O et al., "Fibroblast Growth Factor 23 and Left Ventricular Hypertrophy in Chronic Kidney Disease," Circulation 119(19):2545-2552 (2009).

Hasegawa et al., "Direct Evidence for a Causative Role of FGF23 in the Abnormal Renal Phosphate Handling and Vitamin D Metabolism in Rats with Early-Stage Chronic Kidney Disease," Kidney International 78:975-980 (2010).

Hsu HJ and Wu MS, "Fibroblast Growth Factor 23: A Possible Cause of Left Ventricular Hypertrophy in Hemodialysis Patients," Am. J. Med. Sci. 337(2):116-122 (2009).

Jean et al., "High Levels of Serum Fibroblast Growth Factor (FGF)-23 are Associated with Increased Mortality in Long Haemodialysis Patients," Nephrol. Dial. Transplant 24(9):2792-2796 (2009).

Larsson et al., "Circulating Concentration of FGF-23 Increases as Renal Function Declines in Patients with Chronic Kidney Disease, but Does Not Change in Response to Variation in Phosphate Intake in Healthy Volunteers," Kidney Int. 64(6):2272-2279 (2003).

Mirza et al., "Circulating Fibroblast Growth Factor-23 is Associated with Vascular Dysfunction in the Community," Atherosclerosis 205(2):385-390 (2009).

Mirza et al., "Serum Intact FGF23 Associate with Left Ventricular Mass, Hypertrophy and Geometry in an Elderly Population," Atherosclerosis 207(2):546-551 (2009).

(56) References Cited

OTHER PUBLICATIONS

Mirza et al., "Circulating Fibroblast Growth Factor-23 Is Associated with Fat Mass and Dyslipidemia in Two Independent Cohorts of Elderly Individuals," Arterioscler. Thromb. Vasc. Biol. 31:219-227 (2011).

Nakanishi et al., "Serum Fibroblast Growth Factor-23 Levels Predict the Future Refractory Hyperparathyroidism in Dialysis Patients," Kidney Int. 67(3):1171-1178 (2005).

Nasrallah et al., "Fibroblast Growth Factor-23 (FGF-23) Is Independently Correlated to Aortic Calcification in Haemodialysis Patients," Nephrol. Dial. Transplant 25(8):2679-2685 (2010).

Shigematsu et al., "Possible Involvement of Circulating Fibroblast Growth Factor 23 in the Development of Secondary Hyperparathyroidism Associated with Renal Insufficiency," Am J Kidney Dis 44(2):250-256 (2004).

Westerberg et al., "Regulation of Fibroblast Growth Factor-23 in Chronic Kidney Disease," Nephrol Dial Transplant 22(11):3202-3207 (2007).

International Search Report and Written Opinion for PCT/US2015/023349 (dated Jul. 16, 2015).

Nallamsetty et al., "Gateway Vectors for the Production of Combinatorially-Tagged His6-MBP Fusion Proteins in the Cytoplasm and Periplasm of *Escherichia coli*," Protein Sci. 14:2964-2971 (2005).

Isakova et al., "Fibroblast Growth Factor 23 is Elevated Before Parathyroid Hormone and Phosphate in Chronic Kidney Disease," Kidney International (2011) 79: 1370-1378 (2011).

Andrukhova et al., "FGF23 Drives Progression of Chronic Kidney Disease in Mice," Abstract No. TH-OR105, Kidney Week, Nov. 2015, San Diego, CA.

Shalhoub et al., "FGF23 Neutralization Improves Chronic Kidney Disease-Associated Hyperparathyroidism yet Increases Mortality," J. Clin. Invest. 122(7): 2543-53 (2012).

Leifheit-Nestler et al., "Induction of Cardiac FGF23/FGFR4 Expression is Associated with Left Ventricular Hypertrophy in Patients with Chronic Kidney Disease," Nephrol. Dial. Transplant 31:1088-99 (2016).

Ketteler et al., "Treating Hyperphosphatemia—Current and Advancing Drugs," Expert Opin. Pharmacother. 17:1873-1879 (2016).

Yang et al., "Models of Chronic Kidney Disease," Drug Dis Models. 7(1-2):13-19 (2010).

Hu et al., "Fibroblast Growth Factor 23 and Klotho: Physiology and Pathophysiology of an Endocrine Network of Mineral Metabolism," Annu. Rev. Physiol. 75:503-33 (2013).

Neyra et al., "Fibroblast Growth Factor 23 and Acute Kidney Injury," Pediatr. Nephrol. 30(11):1909-18 (2014).

Notice of Reasons for Rejection in corresponding Japanese Patent Application No. 2017-502954 (dated Feb. 6, 2019).

Examination Report in corresponding European Patent Application No. 15767912.7 (dated Mar. 29, 2019).

\* cited by examiner

C57BL/6 CONTROL
DAY 50

C57BL/6J-Phex$^{Hyp}$/J
CONTROL
DAY 50

C57BL/6J-Phex$^{Hyp}$/J
3 mg/kg/DOSE
DAY 50

C57BL/6J-Phex$^{Hyp}$/J
10 mg/kg/DOSE
DAY 50

SEQUENCE LISTING

```
<160> NUMBER OF SEQ ID NOS: 25

<210> SEQ ID NO 1
<211> LENGTH: 251
<212> TYPE: PRT
<213> ORGANISM: Homo sapiens

<400> SEQUENCE: 1

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
```

His Thr Arg Ser Ala Glu Asp Asp Ser Glu Arg Asp Pro Leu Asn Val
            165                 170                 175

Leu Lys Pro Arg Ala Arg Met Thr Pro Ala Pro Ala Ser Cys Ser Gln
        180                 185                 190

Glu Leu Pro Ser Ala Glu Asp Asn Ser Pro Met Ala Ser Asp Pro Leu
    195                 200                 205

Gly Val Val Arg Gly Gly Arg Val Asn Thr His Ala Gly Gly Thr Gly
210                 215                 220

Pro Glu Gly Cys Arg Pro Phe Ala Lys Phe Ile
225                 230                 235                 240

245                 250

<210> SEQ ID NO 2
<211> LENGTH: 72
<212> TYPE: PRT
<213> ORGANISM: Homo sapiens

<400> SEQUENCE: 2

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
        35                  40                  45

Arg Gly Gly Arg Val Asn Thr His Ala Gly Gly Thr Gly Pro Glu Gly
    50                  55                  60

Cys Arg Pro Phe Ala Lys Phe Ile
65                  70

<210> SEQ ID NO 3
<211> LENGTH: 70
<212> TYPE: PRT
<213> ORGANISM: Artificial
<220> FEATURE:
<223> OTHER INFORMATION: Human FGF23 c-tail 70

<400> SEQUENCE: 3

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
        35                  40                  45

Arg Gly Gly Arg Val Asn Thr His Ala Gly Gly Thr Gly Pro Glu Gly
    50                  55                  60

Cys Arg Pro Phe Ala Lys
65                  70

<210> SEQ ID NO 4
<211> LENGTH: 69
<212> TYPE: PRT
<213> ORGANISM: Artificial
<220> FEATURE:
<223> OTHER INFORMATION: Human FGF23 c-tail 69

<400> SEQUENCE: 4

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro

```
                20                  25                  30

Ser Ala Glu Asp Asn Ser Pro Met Ala Ser Asp Pro Leu Gly Val Val
            35                  40                  45

Arg Gly Gly Arg Val Asn Thr His Ala Gly Gly Thr Gly Pro Glu Gly
        50                  55                  60

Cys Arg Pro Phe Ala
65

<210> SEQ ID NO 5
<211> LENGTH: 67
<212> TYPE: PRT
<213> ORGANISM: Artificial
<220> FEATURE:
<223> OTHER INFORMATION: Human FGF 23 c-tail 67

<400> SEQUENCE: 5

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
            35                  40                  45

Arg Gly Gly Arg Val Asn Thr His Ala Gly Gly Thr Gly Pro Glu Gly
        50                  55                  60

Cys Arg Pro
65

<210> SEQ ID NO 6
<211> LENGTH: 72
<212> TYPE: PRT
<213> ORGANISM: Artificial
<220> FEATURE:
<223> OTHER INFORMATION: Human FGF 23 c-tail 71

<400> SEQUENCE: 6

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
            35                  40                  45

Arg Gly Gly Arg Val Asn Thr His Ala Gly Gly Thr Gly Pro Glu Gly
        50                  55                  60

Cys Arg Pro Phe Ala Lys Phe Gly
65                  70

<210> SEQ ID NO 7
<211> LENGTH: 73
<212> TYPE: PRT
<213> ORGANISM: Artificial
<220> FEATURE:
<223> OTHER INFORMATION: Human FGF 23 c-tail 72

<400> SEQUENCE: 7

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
            35                  40                  45
```

Arg Gly Gly Arg Val Asn Thr His Ala Gly Thr Gly Pro Glu Gly
50                  55                  60

Cys Arg Pro Phe Ala Lys Phe Ile Gly
65                  70

<210> SEQ ID NO 8
<211> LENGTH: 251
<212> TYPE: PRT
<213> ORGANISM: Murine

<400> SEQUENCE: 8

Met Leu Gly Thr Cys Leu Arg Leu Leu Val Gly Val Leu Cys Thr Val
1               5                   10                  15

Cys Ser Leu Gly Thr Ala Arg Ala Tyr Pro Asp Thr Ser Pro Leu Leu
                20                  25                  30

Gly Ser Asn Trp Gly Ser Leu Thr His Leu Tyr Thr Ala Thr Ala Arg
            35                  40                  45

Thr Ser Tyr His Leu Gln Ile His Arg Asp Gly His Val Asp Gly Thr
        50                  55                  60

Pro His Gln Thr Ile Tyr Ser Ala Leu Met Ile Thr Ser Glu Asp Ala
65                  70                  75                  80

Gly Ser Val Val Ile Thr Gly Ala Met Thr Arg Arg Phe Leu Cys Met
                85                  90                  95

Asp Leu His Gly Asn Ile Phe Gly Ser Leu His Phe Ser Pro Glu Asn
                100                 105                 110

Cys Lys Phe Arg Gln Trp Thr Leu Glu Asn Gly Tyr Asp Val Tyr Leu
            115                 120                 125

Ser Gln Lys His His Tyr Leu Val Ser Leu Gly Arg Ala Lys Arg Ile
        130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Gly Pro Ala Ala Ser Asp Pro Leu
210                 215                 220

Gly Val Leu Arg Gly Arg Gly Asp Ala Arg Gly Gly Ala Gly Gly
225                 230                 235                 240

Ala Asp Arg Cys Arg Pro Phe Pro Arg Phe Val
                245                 250

<210> SEQ ID NO 9
<211> LENGTH: 72
<212> TYPE: PRT
<213> ORGANISM: Murine

<400> SEQUENCE: 9

Ser Ala Glu Asp Pro Pro Glu Arg Asp Pro Leu Asn Val Leu Lys Pro
1               5                   10                  15

Arg Pro Arg Ala Thr Pro Val Pro Val Ser Cys Ser Arg Glu Leu Pro
                20                  25                  30

Ser Ala Glu Glu Gly Gly Pro Ala Ala Ser Asp Pro Leu Gly Val Leu
            35                  40                  45

```
Arg Arg Gly Arg Gly Asp Ala Arg Gly Gly Ala Gly Ala Asp Arg
        50                  55                  60

Cys Arg Pro Phe Pro Arg Phe Val
 65                  70
```

<210> SEQ ID NO 10
<211> LENGTH: 12
<212> TYPE: PRT
<213> ORGANISM: Artificial
<220> FEATURE:
<223> OTHER INFORMATION: Linker

<400> SEQUENCE: 10

```
Gly Ser Gly Glu Gly Glu Gly Ser Glu Gly Ser Gly
 1               5                  10
```

<210> SEQ ID NO 11
<211> LENGTH: 12
<212> TYPE: PRT
<213> ORGANISM: Artificial
<220> FEATURE:
<223> OTHER INFORMATION: Linker

<400> SEQUENCE: 11

```
Gly Gly Ser Glu Gly Glu Gly Ser Glu Gly Gly Ser
 1               5                  10
```

<210> SEQ ID NO 12
<211> LENGTH: 5
<212> TYPE: PRT
<213> ORGANISM: Artificial
<220> FEATURE:
<223> OTHER INFORMATION: Linker

<400> SEQUENCE: 12

```
Gly Gly Gly Gly Ser
 1               5
```

<210> SEQ ID NO 13
<211> LENGTH: 232
<212> TYPE: PRT
<213> ORGANISM: Homo sapiens

<400> SEQUENCE: 13

```
Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
         50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
```

```
            130                 135                 140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 14
<211> LENGTH: 232
<212> TYPE: PRT
<213> ORGANISM: Artificial
<220> FEATURE:
<223> OTHER INFORMATION: Human IgG1 FC1

<400> SEQUENCE: 14

Glu Pro Lys Ser Cys Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Leu His Glu Ala Leu His Ser His Tyr Thr Gln Lys
    210                 215                 220

Ser Leu Ser Leu Ser Pro Gly Lys
225                 230

<210> SEQ ID NO 15
<211> LENGTH: 308
<212> TYPE: PRT
```

<213> ORGANISM: Artificial
<220> FEATURE:
<223> OTHER INFORMATION: FGF23-c-tail-FC1

<400> SEQUENCE: 15

```
Glu Pro Lys Ser Cys Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Ser Ala Glu Asp
225                 230                 235                 240

Asp Ser Glu Arg Asp Pro Leu Asn Val Leu Lys Pro Arg Ala Arg Met
                245                 250                 255

Thr Pro Ala Pro Ala Ser Cys Ser Gln Glu Leu Pro Ser Ala Glu Asp
            260                 265                 270

Asn Ser Pro Met Ala Ser Asp Pro Leu Gly Val Val Arg Gly Gly Arg
        275                 280                 285

Val Asn Thr His Ala Gly Gly Thr Gly Pro Glu Gly Cys Arg Pro Phe
    290                 295                 300

Ala Lys Phe Ile
305
```

<210> SEQ ID NO 16
<211> LENGTH: 306
<212> TYPE: PRT
<213> ORGANISM: Artificial
<220> FEATURE:
<223> OTHER INFORMATION: FGF23-c-tail70aa-FC1

<400> SEQUENCE: 16

```
Glu Pro Lys Ser Cys Asp Lys Thr His Thr Cys Pro Pro Cys Pro Ala
1               5                   10                  15
```

```
Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Ser Ala Glu Asp
225                 230                 235                 240

Asp Ser Glu Arg Asp Pro Leu Asn Val Leu Lys Pro Arg Ala Arg Met
                245                 250                 255

Thr Pro Ala Pro Ala Ser Cys Ser Gln Glu Leu Pro Ser Ala Glu Asp
            260                 265                 270

Asn Ser Pro Met Ala Ser Asp Pro Leu Gly Val Val Arg Gly Gly Arg
        275                 280                 285

Val Asn Thr His Ala Gly Gly Thr Gly Pro Glu Gly Cys Arg Pro Phe
    290                 295                 300

Ala Lys
305

<210> SEQ ID NO 17
<211> LENGTH: 305
<212> TYPE: PRT
<213> ORGANISM: Artificial
<220> FEATURE:
<223> OTHER INFORMATION: FGF23-c-tail69aa-FC1

<400> SEQUENCE: 17

Glu Pro Lys Ser Cys Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Ser Ala Glu Asp
225                 230                 235                 240

Asp Ser Glu Arg Asp Pro Leu Asn Val Leu Lys Pro Arg Ala Arg Met
                245                 250                 255

Thr Pro Ala Pro Ala Ser Cys Ser Gln Glu Leu Pro Ser Ala Glu Asp
            260                 265                 270

Asn Ser Pro Met Ala Ser Asp Pro Leu Gly Val Val Arg Gly Gly Arg
        275                 280                 285

Val Asn Thr His Ala Gly Gly Thr Gly Pro Glu Gly Cys Arg Pro Phe
    290                 295                 300

Ala
305

<210> SEQ ID NO 18
<211> LENGTH: 303
<212> TYPE: PRT
<213> ORGANISM: Artificial
<220> FEATURE:
<223> OTHER INFORMATION: FGF23-c-tail67aa-FC1

<400> SEQUENCE: 18

Glu Pro Lys Ser Cys Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
195                 200                 205

Ser Cys Ser Val Met His Glu Ala Leu His Asn His Tyr Thr Gln Lys
            210                 215                 220

Ser Leu Ser Leu Ser Pro Gly Gly Gly Gly Ser Ser Ala Glu Asp
225                 230                 235                 240

Asp Ser Glu Arg Asp Pro Leu Asn Val Leu Lys Pro Arg Ala Arg Met
                245                 250                 255

Thr Pro Ala Pro Ala Ser Cys Ser Gln Glu Leu Pro Ser Ala Glu Asp
            260                 265                 270

Asn Ser Pro Met Ala Ser Asp Pro Leu Gly Val Val Arg Gly Gly Arg
275                 280                 285

Val Asn Thr His Ala Gly Gly Thr Gly Pro Glu Gly Cys Arg Pro
            290                 295                 300

<210> SEQ ID NO 19
<211> LENGTH: 308
<212> TYPE: PRT
<213> ORGANISM: Artificial
<220> FEATURE:
<223> OTHER INFORMATION: FGF23-c-tail71FC1

<400> SEQUENCE: 19

Glu Pro Lys Ser Cys Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Ser Ala Glu Asp
225                 230                 235                 240

Asp Ser Glu Arg Asp Pro Leu Asn Val Leu Lys Pro Arg Ala Arg Met
                245                 250                 255

Thr Pro Ala Pro Ala Ser Cys Ser Gln Glu Leu Pro Ser Ala Glu Asp
            260                 265                 270

Asn Ser Pro Met Ala Ser Asp Pro Leu Gly Val Val Arg Gly Gly Arg
        275                 280                 285

Val Asn Thr His Ala Gly Gly Thr Gly Pro Glu Gly Cys Arg Pro Phe
    290                 295                 300

Ala Lys Phe Gly
305

<210> SEQ ID NO 20
<211> LENGTH: 309
<212> TYPE: PRT
<213> ORGANISM: Artificial
<220> FEATURE:
<223> OTHER INFORMATION: FGF23-c-tail72FC1

<400> SEQUENCE: 20

Glu Pro Lys Ser Cys Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

Ser Leu Ser Leu Ser Pro Gly Gly Gly Gly Ser Ser Ala Glu Asp
225                 230                 235                 240

Asp Ser Glu Arg Asp Pro Leu Asn Val Leu Lys Pro Arg Ala Arg Met
            245                 250                 255

Thr Pro Ala Pro Ala Ser Cys Ser Gln Glu Leu Pro Ser Ala Glu Asp
        260                 265                 270

Asn Ser Pro Met Ala Ser Asp Pro Leu Gly Val Val Arg Gly Gly Arg
            275                 280                 285

Val Asn Thr His Ala Gly Gly Thr Gly Pro Glu Gly Cys Arg Pro Phe
    290                 295                 300

Ala Lys Phe Ile Gly
305

<210> SEQ ID NO 21
<211> LENGTH: 303
<212> TYPE: PRT
<213> ORGANISM: Artificial
<220> FEATURE:
<223> OTHER INFORMATION: muFGF23-c-tail-FC1

<400> SEQUENCE: 21

Val Pro Arg Asp Ala Gly Cys Lys Pro Cys Ile Cys Thr Val Pro Pro
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
        35                  40                  45

Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Ala Phe Ala Cys Ala Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Gly Gly Gly Gly Ser Ser Ala Glu Asp Pro Pro Glu Arg Asp
225                 230                 235                 240

Pro Leu Asn Val Leu Lys Pro Arg Pro Arg Ala Thr Pro Val Pro Val
                245                 250                 255

Ser Cys Ser Arg Glu Leu Pro Ser Ala Glu Glu Gly Gly Pro Ala Ala
            260                 265                 270

```
Ser Asp Pro Leu Gly Val Leu Arg Arg Gly Arg Gly Asp Ala Arg Gly
            275                 280                 285

Gly Ala Gly Gly Ala Asp Arg Cys Arg Pro Phe Pro Arg Phe Val
        290                 295                 300
```

<210> SEQ ID NO 22
<211> LENGTH: 984
<212> TYPE: DNA
<213> ORGANISM: Artificial
<220> FEATURE:
<223> OTHER INFORMATION: Human Wild Type FGF23 c-tail Fc coding sequence

<400> SEQUENCE: 22

```
atgggatgga gctgtatcat cctcttcttg gtggcaacag ctacaggcgt gcactccgag      60
cccaaatctt gtgacaaaac tcacacatgc ccaccgtgcc cagcacctga agccgctggg     120
gcaccgtcag tcttcctctt ccccccaaaa cccaaggaca ccctcatgat ctcccggacc     180
cctgaggtca catgcgtggt ggtggacgtg agccacgaag accctgaggt caagttcaac     240
tggtacgtgg acggcgtgga ggtgcataat gccaagacaa agccgcggga ggagcagtac     300
aacagcacgt accgtgtggt cagcgtcctc accgtcctgc accaggactg gctgaatggc     360
aaggagtaca agtgcaaggt ctccaacaaa gccctcccag cccccatcga aaaaccatc     420
tccaaagcca agggcagcc cgagaaccca ggtgtaca ccctgccccc atcccgggag     480
gagatgacca agaaccaggt cagcctgacc tgcctggtca aaggcttcta tcccagcgac     540
atcgccgtgg agtgggagag caatgggcag ccggagaaca actacaagac cacgcctccc     600
gtgctggact ccgacggctc cttcttcctc tatagcaagc tcaccgtgga caagagcagg     660
tggcagcagg ggaacgtctt ctcatgctcc gtgatgcatg aggctctgca caaccactac     720
acgcagaaga gcctctccct gtccccgggt ggcggagggg gcagcagcgc cgaggacgac     780
tcggagcggg accccctgaa cgtgctgaag cccgggccc ggatgacccc ggccccggcc     840
tcctgttcac aggagctccc gagcgccgag acaacagcc cgatggccag tgacccatta     900
ggggtggtca gggcggtcg agtgaacacg cacgctgggg gaacgggccc ggaaggctgc     960
cgccccttcg ccaagttcat ctga                                            984
```

<210> SEQ ID NO 23
<211> LENGTH: 327
<212> TYPE: PRT
<213> ORGANISM: Artificial
<220> FEATURE:
<223> OTHER INFORMATION: Human Wild Type FGF23 C-Tail Fc Precursor Amino
      Acid Sequence

<400> SEQUENCE: 23

```
Met Gly Trp Ser Cys Ile Ile Leu Phe Leu Val Ala Thr Ala Thr Gly
1               5                   10                  15

Val His Ser Glu Pro Lys Ser Cys Asp Lys Thr His Thr Cys Pro Pro
            20                  25                  30

Cys Pro Ala Pro Glu Ala Ala Gly Ala Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95
```

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Gly Gly Gly Ser Ser
                245                 250                 255

Ala Glu Asp Asp Ser Glu Arg Asp Pro Leu Asn Val Leu Lys Pro Arg
            260                 265                 270

Ala Arg Met Thr Pro Ala Pro Ala Ser Cys Ser Gln Glu Leu Pro Ser
        275                 280                 285

Ala Glu Asp Asn Ser Pro Met Ala Ser Asp Pro Leu Gly Val Val Arg
    290                 295                 300

Gly Gly Arg Val Asn Thr His Ala Gly Gly Thr Gly Pro Glu Gly Cys
305                 310                 315                 320

Arg Pro Phe Ala Lys Phe Ile
                325

```
<210> SEQ ID NO 24
<211> LENGTH: 969
<212> TYPE: DNA
<213> ORGANISM: Artificial
<220> FEATURE:
<223> OTHER INFORMATION: Murine Wild Type FGF23 c-tail Fc coding
      sequence

<400> SEQUENCE: 24
atgggatgga gctgtatcat cctcttcttg gtggcaacag ctacaggcgt gcactccgtg     60
cccagggatg ccggttgtaa gccttgcata tgtacagtcc caccagtatc atctgtcttc    120
atcttccccc caaagcccaa ggatgtgctc accattactc tgactcctaa ggtcacgtgt    180
gttgtggtag acatcagcaa ggatgatccc gaggtccagt tcagctggtt tgtagatgat    240
gtggaggtgc acacagctca gacgcaaccc cgggaggagc agttcaacag cactttccgc    300
tcagtcagtg aacttcccat catgcaccag gactggctca atggcaaggc cttcgcatgc    360
gcggtcaaca gtgcagcttt ccctgccccc atcgagaaaa ccatctccaa aaccaaaggc    420
agaccgaagg ctccacaggt gtacaccatt ccacctccca aggagcagat ggccaaggat    480
aaagtcagtc tgacctgcat gataacagac ttcttccctg aagacattac tgtggagtgg    540
cagtggaatg ggcagccagc ggagaactac aagaacactc agcccatcat ggacacagat    600
ggctcttact tcgtctacag caagctcaat gtgcagaaga gcaactggga ggcaggaaat    660
actttcacct gctctgtgtt acatgagggc ctgcacaacc accatactga gaagagcctc    720
```

```
tcccactctc ctggtggcgg aggggcagc agcgccgagg acccacccga gcgcgaccca        780
ctgaacgtgc tcaagccgcg gccccgcgcc acgcctgtgc ctgtatcctg ctctcgcgag        840
ctgccgagcg cagaggaagg tggccccgca gccagcgatc tctgggggt gctgcgcaga        900 ggccgtggag atgctcgcgg gggcgcggga ggcgcggata ggtgtcgccc ctttcccagg        960
ttcgtctag                                                               969
```

```
<210> SEQ ID NO 25
<211> LENGTH: 322
<212> TYPE: PRT
<213> ORGANISM: Artificial
<220> FEATURE:
<223> OTHER INFORMATION: Murine Wild Type FGF23 C-Tail Fc Precursor
      Amino Acid Sequence

<400> SEQUENCE: 25

Met Gly Trp Ser Cys Ile Ile Leu Phe Leu Val Ala Thr Ala Thr Gly
1               5                   10                  15

Val His Ser Val Pro Arg Asp Ala Gly Cys Lys Pro Cys Ile Cys Thr
            20                  25                  30

Val Pro Pro Val Ser Ser Val Phe Ile Phe Pro Pro Lys Pro Lys Asp
        35                  40                  45

Val Leu Thr Ile Thr Leu Thr Pro Lys Val Thr Cys Val Val Val Asp
    50                  55                  60

Ile Ser Lys Asp Asp Pro Glu Val Gln Phe Ser Trp Phe Val Asp Asp
65                  70                  75                  80

Val Glu Val His Thr Ala Gln Thr Gln Pro Arg Glu Glu Gln Phe Asn
                85                  90                  95

Ser Thr Phe Arg Ser Val Ser Glu Leu Pro Ile Met His Gln Asp Trp
            100                 105                 110

Leu Asn Gly Lys Ala Phe Ala Cys Ala Val Asn Ser Ala Ala Phe Pro
        115                 120                 125

Ala Pro Ile Glu Lys Thr Ile Ser Lys Thr Lys Gly Arg Pro Lys Ala
    130                 135                 140

Pro Gln Val Tyr Thr Ile Pro Pro Lys Glu Gln Met Ala Lys Asp
145                 150                 155                 160

Lys Val Ser Leu Thr Cys Met Ile Thr Asp Phe Phe Pro Glu Asp Ile
                165                 170                 175

Thr Val Glu Trp Gln Trp Asn Gly Gln Pro Ala Glu Asn Tyr Lys Asn
            180                 185                 190

Thr Gln Pro Ile Met Asp Thr Asp Gly Ser Tyr Phe Val Tyr Ser Lys
        195                 200                 205

Leu Asn Val Gln Lys Ser Asn Trp Glu Ala Gly Asn Thr Phe Thr Cys
    210                 215                 220

Ser Val Leu His Glu Gly Leu His Asn His His Thr Glu Lys Ser Leu
225                 230                 235                 240

Ser His Ser Pro Gly Gly Gly Gly Ser Ala Glu Asp Pro Pro
                245                 250                 255

Glu Arg Asp Pro Leu Asn Val Leu Lys Pro Arg Pro Arg Ala Thr Pro
            260                 265                 270

Val Pro Val Ser Cys Ser Arg Glu Leu Pro Ser Ala Glu Glu Gly Gly
        275                 280                 285

Pro Ala Ala Ser Asp Pro Leu Gly Val Leu Arg Arg Gly Arg Gly Asp
    290                 295                 300
```

-continued

```
Ala Arg Gly Gly Ala Gly Gly Ala Asp Arg Cys Arg Pro Phe Pro Arg
305                 310                 315                 320

Phe Val
```

FGF23 C-TAIL FUSION PROTEINS

This application is a national stage application under 35 U.S.C. § 371 of PCT Application No. PCT/US2015/023349, filed Mar. 30, 2015, which claims priority benefit of U.S. Provisional Patent Application Ser. No. 61/972,081, filed Mar. 28, 2014, each of which is hereby incorporated by reference in its entirety.

FIELD OF THE INVENTION

The present invention relates to recombinant FGF23 fusion proteins. The invention further relates to compositions comprising such fusion proteins, and the use of these fusion proteins to treat diseases or disorders mediated by FGF23 or fragments thereof.

BACKGROUND OF THE INVENTION

Fibroblast growth factor 23 (FGF23), is an endocrine regulator of mineral ion homeostasis and vitamin D metabolism that is primarily expressed by osteocytes in the bone (Yu and White, (2005) Cytokine Growth Factor Rev 16:221-232; Razzaque, (2009) Nature Rev Endocrinol 5:611-619; Quarles, (2012) Nature Rev Endocrinol 8:276-286). Elevated levels of FGF23 lead to hypophosphatemia (Larsson et al, (2004) Endocrinology 145(7):3087-94; Bai, (2003) J Biol Chem. 278(11):9843-9.; Bai, (2004) Endocrinology. 145(11):5269-79; Shimada, (2004) J Clin Invest. 113(4):561-8; Shimada et al (2001) Proc Natl Acad Sci USA. 98(11):6500-5) and FGF23 levels are elevated in multiple hypophosphatemic diseases.

To date, the best understood function of FGF23 is to decrease serum phosphate and 1,25-dihydroxyvitamin D3 (1,25 VitD) levels (Razzaque, (2009) Nature Rev Endocrinol 5:611-619; Bergwitz, (2010) Annu Rev Med. 61:91-104; Quarles, (2012) Nature Rev Endocrinol 8:276-286). Under normal conditions FGF23 acts in a classic feedback loop, where levels rise in response to an increase in serum phosphate or 1,25 VitD. Mechanistically, FGF23 regulates phosphate by downregulation of the sodium phosphate transporters in the proximal tubule of the kidney (Shimada, (2004); Gattineni, (2009) Am J Physiol Renal Physiol. 297(2):F282-91), thereby increasing renal phosphate excretion. Suppression of 1,25 VitD is achieved through modulation of enzymes responsible for the biosynthesis and degradation of Vitamin D (Larsson, (2004); Bai, (2003); Bai, (2004); Shimada, (2004)). FGF23, like parathyroid hormone (PTH), also promotes renal calcium reabsorption (Andrukhova et al, (2014) EMBO J 33:229-246), and through yet to be identified mechanisms regulates PTH (Krajisnik et al, (2007) J Endocrinol 195:125-131; Bergwitz, (2010) Annu Rev Med. 61:91-104).

FGF23 mediated regulation of both the phosphate and 1,25VitD pathways is dependent on signaling through FGF receptor (FGFR)/α-klotho complexes (Li, (2011) Am J Physiol Endocrinol Metab. 300(3):E508-17; Gattineni, (2011) Am J Physiol Renal Physiol. 301(2):F371-7; Gattineni, (2009); Kurosu, (2006) J Biol Chem. 281(10):6120-3; Urakawa, (2006) Nature. 444(7120):770-4). FGF23 possesses poor binding affinity for FGF receptors (FGFRs) alone, with KDs ranging from 200-700 nM. However, the presence of the co-receptor α-klotho converts FGF23 binding to high affinity, as exemplified by the conversion of a 648 nM affinity between FGF23-FGFR1c to an affinity of 27 nM for FGF23-FGFR1c/αklotho (Goetz, (2012) J Biol Chem. 287(34):29134-46). While FGFRs are ubiquitously expressed in mammalian tissues, αKlotho expression is restricted to specific tissues and this limited expression pattern of aKlotho provides target organ specificity for FGF23. Gene knockout studies in mice have shown that FGFR1c/aKlotho and FGFR4/αKlotho complexes mediate the phosphaturic action of FGF23, albeit to different degrees (Gattineni et al, (2009) Am J Physiol 297:F282-F291; Gattineni et al, (2014) Am J Physiol 306:F351-F358); and FGFR3c/aKlotho and FGFR$^4$/αKlotho complexes predominantly, but not solely, mediate the effects of FGF23 on vitamin D metabolism (Li et al, (2011) Am J Physiol 300:E508-E517; Gattineni et al, (2011) Am J Physiol 301: F371-F377).

As indicated above, FGF23 is a primary modulator of phosphate levels. Indeed both FGF23 deficiency and overexpression lead to distinct disease states, hyperphosphatemia and hypophosphatemia respectively, which manifest as soft tissue mineralization and osteomalacia respectively. Targeting the FGF23 pathway therapeutically requires partial inhibition, so as not to replace one disease state for another. The difficulty in achieving a balance between efficacy and safety was demonstrated in a recent pre-clinical study in which hyperparathyroidism in the context of chronic kidney disease was treated via FGF23 neutralization (Shalhoub, (2012) J Clin Invest. 122(7):2543-53). In this study, efficacy was achieved but only at the expense of increased mortality due to aortic calcification. It was concluded that the efficacy of such treatment would be limited due to increased mineral disturbances.

FGF23 is elevated in X-linked Hypophosphatemia (XLH), the most common of the phosphate wasting diseases which affects approximately 1:20,000 people worldwide (Carpenter, (2011) J Bone Miner Res. 26(7):1381-1388). The disease is characterized by low serum phosphate, inappropriately low levels of 1,25 VitD in the face of hypophosphatemia and poor bone mineralization. XLH is typically diagnosed in children upon the appearance of a distinctive bow-legging phenotype, a consequence of the children's 'soft-bones' inability to bear weight as they begin to walk. Other disease manifestations include growth retardation, bone deformation, fractures and bone pain which continue into adulthood. Many patients undergo multiple invasive surgeries during childhood. The current standard of care for these patients mandates patients take phosphate and calcitriol (the active form of VitD) orally (Carpenter, (2011) J Bone Miner Res. 26(7):1381-1388; Linglart et al., (2014) Endocrine Connections 14:R13-R30). In an attempt to normalize height some children are given growth hormone as well, though this may only exacerbate bone deformities.

The disease heterogeneity across patients requires that each patient have a personalized dosing regimen. Phosphate is given to promote bone improvement but continual activation of this pathway leads to hyperparathyroidism. Calcitriol is given to combat the hyperparathyroidism but can lead to an increased serum calcium-phosphate product, subsequently resulting in tissue mineralization, a potentially serious and irreversible condition. In addition, oral treatment is not well tolerated, resulting in large number of adult patients electing to stop treatment, a choice that can lead to pseudo-fractures and increased bone pain. Clearly, XLH patients have a need for a more causative, more efficacious, and safer therapy. A significant issue with the current standard of care is that it does not treat the cause of disease; elevated FGF23 levels (Larsson, (2004); Bai, (2003); Bai, (2004); Shimada, (2004); Shimada, (2001).

SUMMARY OF THE INVENTION

This application discloses fusion proteins comprising a FGF-23 c-tail protein fused to a heterologous amino acid sequence, wherein said fusion protein modulates serum phosphate levels but does not substantially modulate serum 1,25 VitD levels. In some embodiments, the FGF-23 c-tail protein is fused to the heterologous amino acid sequence via a linker. In exemplary embodiments, the linker may be selected from GSGEGEGSEGSG (SEQ ID NO:10); GGSEGEGSEGGS (SEQ ID NO:11); and GGGGS (SEQ ID NO:12).

In further embodiments, the heterologous amino acid sequence of the fusion protein may comprise a human IgG1 Fc domain. In some embodiments, the Fc domain comprises the amino acid sequence of SEQ ID NO:13. In other embodiments, the Fc domain is modified to alter the effector function of the domain and may comprise the amino acid sequence of SEQ ID NO:14.

In some embodiments, the FGF23 c-tail Fc fusion protein may be selected from an FGF23 c-tail Fc fusion protein comprising an amino acid sequence selected from the group consisting of SEQ ID NO:15, SEQ ID NO:16, SEQ ID NO:17, SEQ ID NO:18, SEQ ID NO:19, and SEQ ID NO:20.

This application also discloses pharmaceutical compositions comprising the modified FGF23 c-tail Fc fusion proteins disclosed herein, and a pharmaceutically acceptable agent.

This application also discloses isolated nucleic acids encoding the FGF23 c-tail Fc fusion proteins disclosed herein. In a specific embodiment, the isolated nucleic acid comprises the nucleotide sequence of SEQ ID NO:22. This invention also encompasses vectors comprising the nucleic acids disclosed herein, and a host cell comprising the vector or polynucleotides encoding the proteins of the invention.

This application also discloses methods of treating a disease or disorder mediated by the interaction of FGF23 with an FGFR/α-klotho complex comprising administering to a patient in need thereof a pharmaceutical composition comprising FGF23 c-tail Fc fusion proteins disclosed herein. The FGF23-mediated disorder may be a hypophosphatemic disorder, including a disorder selected from the group consisting of autosomal dominant hypophosphatemic rickets (ADHR), X-linked hypophosphatemic rickets (XLH), tumor-induced osteomalacia (TIO), fibrous dysplasia (FD), and chronic kidney disease (CKD).

This application also discloses use of the FGF23 c-tail Fc fusion proteins disclosed herein in the manufacture of a medicament for treatment of a disease or disorder mediated by the interaction of FGF23 with an FGFR/α-klotho complex, as well as use of the FGF23 c-tail Fc fusion proteins, and pharmaceutical compositions thereof, for use in treatment of a disease or disorder mediated by the interaction of FGF23 with an FGFR/α-klotho complex in a patient in need thereof. The FGF23-mediated disorder may be a hypophosphatemic disorder, including a disorder selected from the group consisting of autosomal dominant hypophosphatemic rickets (ADHR), X-linked hypophosphatemic rickets (XLH), tumor-induced osteomalacia (TIO), fibrous dysplasia (FD), and chronic kidney disease (CKD).

This application also discloses use of the FGF23 c-tail Fc fusion proteins disclosed herein in methods of treating left ventricular hypertrophy or hyperparathyroidism comprising administering to a patient in need thereof a pharmaceutical composition comprising FGF23 c-tail Fc fusion proteins disclosed herein. This application also discloses the use of the FGF23 c-tail Fc fusion proteins disclosed herein in the manufacture of a medicament for treatment of left ventricular hypertrophy or hyperparathyroidism, as well as use of the FGF23 c-tail Fc fusion proteins, and pharmaceutical compositions thereof, for use in treatment of left ventricular hypertrophy or hyperparathyroidism.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s) which are presently preferred. It should be understood, however, that the invention is not limited to the precise arrangements and instrumentalities shown.

In the drawings:

FIG. 2, comprising panels A and B, shows images of a SDS PAGE gel of FGF23 c-tail fusion construct FGF23-c-tail-FC1.

FIG. 4, comprising panels A and B, depicts graphs showing the Intact Mass analysis FGF23-c-tail-FC1.

FIG. 6, comprising panels A, B, C, and D depicts graphs illustrating inhibition by the FGF23 c-tail Fc fusion of FGF23 signaling in HEK293-aKlotho cells using an Egr1-luciferase reporter assay.

FIG. 8, comprising panels A and B, shows graphs depicting serum chemistry analysis performed 24 hrs post the 5$^{th}$ dose in wild-type rats.

FIG. 11, comprising panels A-D, shows images demonstrating the lack of renal tissue mineralization following 7 weeks of dosing of Hyp animals with phosphate buffer, 3 mg/kg of muFGF23 c-tail Fc, 10 mg/kg murine FGF23 c-tail Fc, and wild-type mice treated with phosphate buffer. Shown are images visualizing the left kidney visualized ex vivo as imaged by Faxitron X-ray.

FIG. 13, comprising panels A-D, shows images demonstrating the improvement in bone mineralization and structure after treatment of Hyp animals with 10 mg/kg muFGF23 c-tail Fc following 7 weeks of dosing. FIG. 13 shows images visualizing the cancellous bone of the distal femoral metaphysis as imaged by ex vivo pCT.

FIG. 14, comprising panels A-D, shows images demonstrating the improvement in bone mineralization and structure after treatment of Hyp animals with 10 mg/kg muFGF23 c-tail Fc following 7 weeks of dosing. FIG. 14 depicts bone quality as imaged via three-dimensional space filling analysis using pCT.

FIG. 15, comprising panels A-D, shows images demonstrating the dose responsive improvement in bone architecture after treatment with muFGF23 c-tail Fc following 7 weeks of dosing. Hematoxylin and Eosin staining of tibial physes depicts bone architecture.

FIG. 16, comprising panels A and B, are graphs showing serum concentrations of huFGF23 c-tail Fc in Cynomolgus monkeys and Rats as a function of time.

FIG. 17, comprising panels A and B, shows graphs illustrating results of preliminary competition binding experiments on BaF3 cells ectopically expressing aKlotho and cognate FGFRs of FGF23.

DETAILED DESCRIPTION OF THE INVENTION

Figure 1:
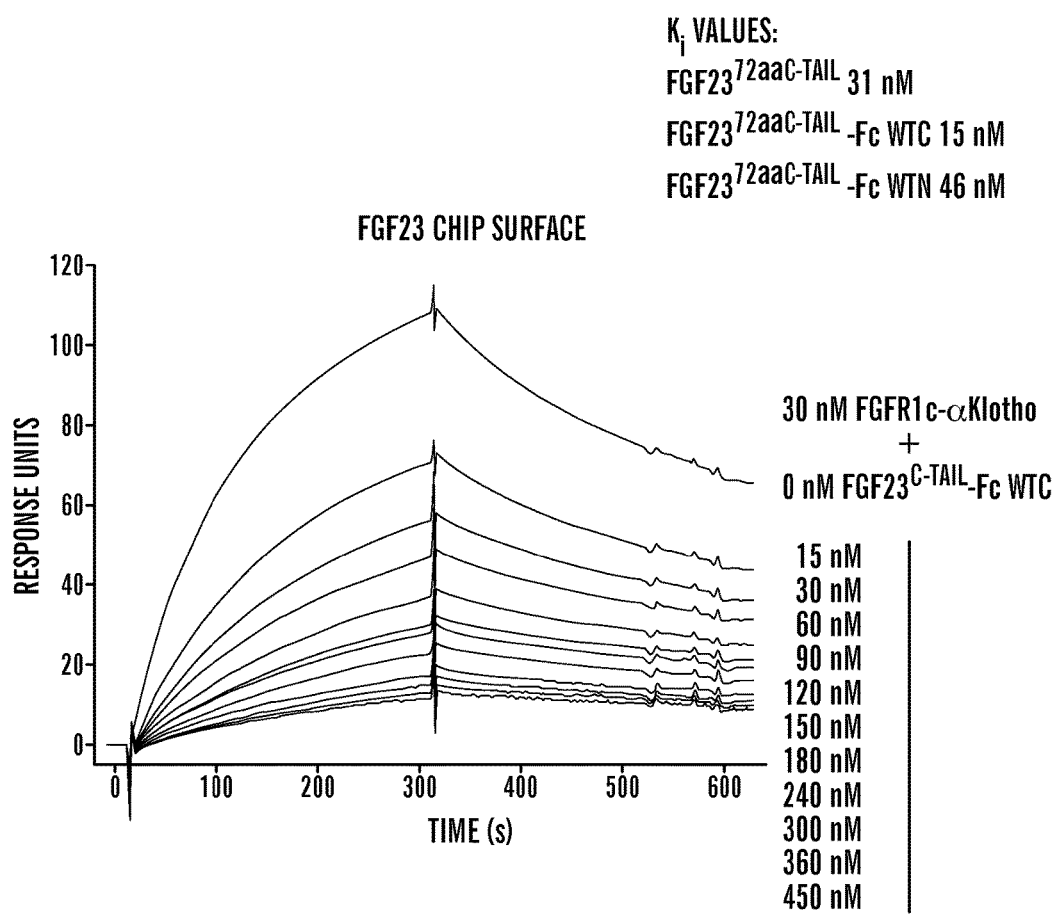
FIG. 1, shows graphs depicting the ability of FGF 23 c-tail fused at the C-terminus of an effectorless Fc to competitively inhibit the binding of FGF23 to the FGFR1c/α-klotho receptor complex as measured by SPR.

This application discloses FGF23 c-tail fusion proteins with improved properties, including greater improved stability, increased half-life, partial inhibition of the activity of the full-length FGF23 protein, and selective modulation of serum phosphate levels as opposed to modulation of serum 1,25VitD levels.

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual*, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "FGF23 c-tail", "c-tail" or "FGF23 c-terminal peptide" as used herein, refers to the 72 amino acid c-terminal peptide, or fragments thereof, generated after FGF23 is proteolytic cleavage. The FGF23 c-tail of the present invention may comprise a peptide comprising 26 to 72 amino acids.

The term "vitamin D" as used herein is meant to include all forms of vitamin D2 and vitamin D3. In one embodiment, the analyte is 25-hydroxy vitamin D3, 25-hydroxy vitamin D2, or 1,25-dihydroxyvitaminD3 (1,25-dihydroxycholecalciferol). The term "1,25-dihydroxyvitamin D3", "1,25-dihydroxycholecalciferol" or "1,25VitD" as used herein is meant to refer to the hormonally active form of vitamin D.

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation has one to four of the following: (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxyterminal deletion, but where the remaining amino acid sequence is identical to the corresponding positions in the full-length naturally-occurring sequence. Also, fragments according to the invention may be made by truncation, e.g., by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "dimerization domain" as used herein refers to the protein domain which enables spontaneous dimerization of embodiments of the FGF 23 c-tail fusion proteins described herein. Dimerization domains enabling spontaneous dimerization include but are not limited to leucine zipper, zinc finger domain, or cysteine knot domains.

In certain embodiments, amino acid substitutions of a protein or portion thereof are those which: (1) reduce susceptibility to proteolysis, (2) reduce susceptibility to oxidation, (3) alter binding affinity for forming protein complexes, or (4) confer or modify other physicochemical or functional properties. For example, single or multiple amino acid substitutions (preferably conservative amino acid substitutions) may be made in the normally-occurring sequence.

A conservative amino acid substitution should not substantially change the structural characteristics of the parent sequence. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), which are each incorporated herein by reference.

The term "binding affinity ($K_D$)" as used herein, is intended to refer to the dissociation rate of a particular antigen-antibody or protein-receptor interaction. The $K_D$ is the ratio of the rate of dissociation, also called the "off-rate ($k_{off}$)", to the association rate, or "on-rate ($k_{on}$)". Thus, $K_D$ equals $K_{off}/k_{on}$ and is expressed as a molar concentration (M). It follows that the smaller the $K_D$, the stronger the affinity of binding. Therefore, a $K_D$ of 1 µM indicates weaker binding affinity compared to a $K_D$ of 1 nM. $K_D$ values for antibodies can be determined using methods well established in the art. One method for determining the $K_D$ is by using surface plasmon resonance, typically using a biosensor system such as a BIAcore® system.

The term "surface plasmon resonance" (SPR), as used herein, refers to an optical phenomenon that allows for the analysis of real-time biospecific interactions by detection of alterations in protein concentrations within a biosensor matrix, for example using the BIACORE™ system (formerly Pharmacia Biosensor AB, Uppsala, Sweden acquired by GE Healthcare, Little Chalfont, UK). For further descriptions, see Jonsson U. et al., *Ann. Biol. Clin.* 51:19-26 (1993); Jonsson U. et al., *Biotechniques* 11:620-627 (1991); Jonsson B. et al., *J. Mol. Recognit.* 8:125-131 (1995); and Johnsson B. et al., *Anal. Biochem.* 198:268-277 (1991).

As used herein, the twenty naturally occurring amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference.

The term "polynucleotide" as referred to herein means a polymeric form of nucleotides of at least 10 bases in length, either ribonucleotides or deoxyribonucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin or source of derivation, the "isolated polynucleotide" has one to three of the following: (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "oligonucleotide" as used herein includes naturally occurring, and modified nucleotides linked together by naturally occurring and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for primers and probes; although oligonucleotides may be double stranded, e.g. for use in the construction of a gene mutant. Oligonucleotides of the invention can be either sense or antisense oligonucleotides.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides* and *Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded DNA loop into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which an exogenous nucleic acid and/or recombinant vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleic acid sequences means the percent of residues when a first contiguous sequence is compared and aligned for maximum correspondence to a second contiguous sequence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleotide sequence encompasses its complement unless otherwise specified. Thus, a reference to a nucleic acid having a particular sequence should be understood to encompass its complementary strand, with its complementary sequence.

The term "percent sequence identity" means a ratio, expressed as a percent of the number of identical residues over the number of residues compared.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, 91%, 92%, 93%, 94%, 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights, as supplied with the programs, share at least 70%, 75%, 80% or 85% sequence identity, preferably at least 90%, 91%, 92%, 93%, 94% 95%, 96%, 97%, 98% or 99% sequence identity. In certain embodiments, residue positions that are not identical differ by conservative amino acid substitutions.

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.* 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Alternatively, a conservative substitution or replacement, as the terms are used interchangeably herein, is any change having a positive value in the PAM250 log-likelihood matrix disclosed in Gonnet et al., *Science* 256:1443-45 (1992), herein incorporated by reference. A "moderately conservative" replacement is any change having a nonnegative value in the PAM250 log-likelihood matrix.

Sequence identity for polypeptides, is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters, as specified with the programs, to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, see GCG Version 6.1. (University of Wisconsin Wis.) FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters, as supplied with the programs. See, e.g., Altschul et al., *J. Mol. Biol.* 215:403-410 (1990); Altschul et al., *Nucleic Acids Res.* 25:3389-402 (1997).

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

The term "potency" is a measurement of biological activity and may be designated as $IC_{50}$, or effective concentration of a protein needed to inhibit 50% of a biological activity in a cell which activity is mediated by the protein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "substantially modulate", when referring to a serum concentration of 1,25VitD, as used herein, refers to an increase in serum concentration of at least 2 fold or a decrease in serum concentration of at least 2 fold as compared to baseline values.

The term "modulate", when referring to a serum concentration of phosphate, as used herein, refers to a statistically significant increase in serum concentration above baseline hypophoshatemic levels.

The term "inhibit" or "neutralize" as used herein with respect to bioactivity of a polypeptide of the invention means the ability of the polypeptide to substantially antagonize, prohibit, prevent, restrain, slow, disrupt, eliminate, stop, reduce or reverse e.g. progression or severity of that which is being inhibited including, but not limited to, a biological activity.

The term "compete", as used herein with regard to polypeptide, means that a first polypeptide binds to a ligand in a manner sufficiently similar to the binding of a second polypeptide such that the result of binding of the first polypeptide with its cognate ligand is detectably decreased in the presence of the second polypeptide compared to the binding of the first polypeptide in the absence of the second polypeptide. The alternative, where the binding of the second polypeptide to its ligand is also detectably decreased in the presence of the first polypeptide, can, but need not be the case. That is, a first polypeptide can inhibit the binding of a second polypeptide to its ligand without that second polypeptide inhibiting the binding of the first polypeptide to its respective ligand. However, where each polypeptide detectably inhibits the binding of the other polypeptide with its cognate ligand, whether to the same, greater, or lesser extent, the polypeptides are said to "cross-compete" with each other for binding of their respective ligand(s). Both competing and cross-competing polypeptides are encompassed by the present invention. Regardless of the mechanism by which such competition or cross-competition occurs (e.g., steric hindrance, conformational change, or binding to a common ligand, or portion thereof), the skilled artisan would appreciate, based upon the teachings provided herein, that such competing and/or cross-competing polypeptides are encompassed and can be useful for the methods disclosed herein.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic folding topology. The known Ig domains in the IgG class of antibodies are the variable heavy chain domain (VH), the heavy chain constant domains—Cγ1, Cγ2, Cγ3—together comprising the Cγ domain which includes the hinge region between Cγ1 and Cγ2, the variable domain of the light chain (VL), and the constant domain of the light chain (CL), which in humans comprises either the kappa (CO or lambda (CA) light chain constant domain.

As known in the art, the term "Fc region" is used to define a C-terminal region of an immunoglobulin heavy chain. The "Fc region" (also known as the "fragment crystallizable" or "tail" region) may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. For all heavy chain constant region amino acid positions discussed in the present invention, numbering is according to the EU index first described in Edelman et al., 1969, Proc. Natl. Acad. Sci. USA 63(1):78-85, describing the amino acid sequence of myeloma protein EU, which is the first human IgG1 sequenced. The EU index of Edelman et al. is also set forth in Kabat et al., Sequences of Proteins of Immunological Interest, 5th Ed. Public Health Service, National Institutes of Health, Bethesda, Md., 1991. Thus, the "EU index as set forth in Kabat" or "EU index of Kabat" refers to the amino acid residue numbering system based on the human IgG1 EU antibody of Edelman et al. as set forth in Kabat 1991.

The Fc region of an immunoglobulin generally comprises two constant domains, CH2 and CH3. Typically, an "Fc polypeptide," as the term is used herein, comprises a CH2 and a CH3 domain and can include at least a portion of the hinge domain, but does not usually include the entire CH1 domain. As is known in the art, an Fc region can be present in dimeric or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

As used herein, "pharmaceutically acceptable carrier" or "pharmaceutical acceptable excipient" includes any material which, when combined with an active ingredient, allows the ingredient to retain biological activity and is non-reactive with the subject's immune system. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment.

FGF23 Proteins

FGF23 is inactivated in vivo by site-specific proteolytic cleavage at an $^{176}$RXXR$^{179}$ motif, which yields a C-terminal (c-tail) and an N-terminal fragment (Shimada, (2002); White, (2001) Kidney Int. 60(6):2079-86; Goetz et al., (2007) Mol Cell Biol, 27(9):3417-28; Goetz et al., (2010) Proc Natl Acad Sci USA 107:407-412). The C-terminal proteolytic fragment, FGF23 c-tail, which contains the binding site of FGF23 for the binary FGFR/aKlotho complex, can effectively compete with full-length FGF23 for binding to the binary receptor complex but, in contrast to the full length ligand, does not induce receptor activation (Goetz et al., (2010) Proc Natl Acad Sci USA 107:407-412). Thus the proteolytic cleavage inactivates FGF23 by two mechanisms; by removing the binding site for the binary receptor complex from FGF23 and by generating an endogenous competitive antagonist to FGF23. However, the half-life of the 72aa c-tail peptide is prohibitively short with an estimated half-life of 10 minutes (Goetz et al., (2010) Proc Natl Acad Sci USA 107:407-412).

Table 1 provides the complete sequences of various FGF23 and FGF23 c-tail proteins.

TABLE 1

FGF23 and FGF23 c-tail Sequences

| Description | Amino Acid Sequence | SEQ ID NO. |
|---|---|---|
| Wild Type Human FGF23 (RXXR cleavage motif in bold and underlined) | MLGARLRLWVCALCSVCSMSVLRAYPNAS PLLGSSWGGLIHLYTATARNSYHLQIHKN GHVDGAPHQTIYSALMIRSEDAGFVVITG VMSRRYLCMDFRGNIFGSHYFDPENCRFQ HQTLENGYDVYHSPQYHPLVSLGRAKRAF LPGMNPPPYSQFLSRRNEIPLIHFNTPIP RRHTRSAEDDSERDPLNVLKPRARMTPAP ASCSQELPSAEDNSPMASDPLGVVRGGRV NTHAGGTGPEGCRPFAKFI | 1 |
| Wild Type Human FGF23 c-tail[180-251] | SAEDDSERDPLNVLKPRARMTPAPASCSQ ELPSAEDNSPMASDPLGVVRGGRVNTHAG GTGPEGCRPFAKFI | 2 |
| Human FGF23 c-tail 70 (-2 amino acid construct) | SAEDDSERDPLNVLKPRARMTPAPASCSQ ELPSAEDNSPMASDPLGVVRGGRVNTHAG GTGPEGCRPFAK | 3 |
| Human FGF23 c-tail 69 (-3 amino acid construct) | SAEDDSERDPLNVLKPRARMTPAPASCSQ ELPSAEDNSPMASDPLGVVRGGRVNTHAG GTGPEGCRPFA | 4 |
| Human FGF 23 c-tail 67 (-5 amino acid construct) | SAEDDSERDPLNVLKPRARMTPAPASCSQE LPSAEDNSPMASDPLGVVRGGRVNTHAGGT GPEGCRP | 5 |
| Human FGF 23 c-tail 71 + G (71 amino acid + G construct) | SAEDDSERDPLNVLKPRARMTPAPASCSQE LPSAEDNSPMASDPLGVVRGGRVNTHAGGT GPEGCRPFAKFG | 6 |
| Human FGF 23 c-tail 72 + G (72 amino acid + G construct) | SAEDDSERDPLNVLKPRARMTPAPASCSQE LPSAEDNSPMASDPLGVVRGGRVNTHAGGT GPEGCRPFAKFIG | 7 |
| Wild Type Murine FGF 23 (RXXR cleavage motif in bold and underlined) | *MLGTCLRLLVGVLCTVCSLGTARAYPDTSP LLGSNWGSLTHLYTATARTSYHLQIHRDGH VDGTPHQTIYSALMITSEDAGSVVITGAMT RRFLCMDLHGNIFGSLHFSPENCKFRQWTL ENGYDVYLSQKHHYLVSLGRAKRIFQPGTN PPPFSQFLARRNEVPLLHFYTVRPRRHTRS AEDPPERDPLNVLKPRPRATPVPVSCSREL PSAEEGGPAASDPLGVLRRGRGDARGGAGG ADRCRPFPRFV* | 8 |
| Wild Type Murine FGF23 c-tail | SAEDPPERDPLNVLKPRPRATPVPVSCSRE LPSAEEGGPAASDPLGVLRRGRGDARGGAG GADRCRPFPRFV | 9 |

FGF23 c-tail Fusion Proteins

This application discloses FGF23 c-tail fusion proteins having substantially improved useful characteristics. Such fusion proteins may be used, for example, as antagonists of FGF23 activity.

As used herein, the term "FGF23 c-tail fusion polypeptide", "FGF23 c-tail fusion protein" or "FGF23 c-tail Fc" refers to a fusion of one or more amino acid residues (such as a heterologous protein or peptide) at the N-terminus or C-terminus of any FGF23 c-tail proteins described herein. Thus, the term "fusion protein" refers to a protein or polypeptide that has an amino acid sequence derived from two or more proteins. The fusion protein may also include linking regions of amino acids between amino acid portions derived from separate proteins.

Heterologous peptides and polypeptides include, but are not limited to, an epitope (e.g., FLAG) or a tag sequence (e.g., His$_6$, and the like) to allow for the detection and/or isolation of an FGF23 c-tail protein; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region (e.g., an Fc domain); a half life-extending sequence comprising a combination of two or more (e.g., 2, 5, 10, 15, 20, 25, etc) naturally occurring or non-naturally occurring charged and/or uncharged amino acids (e.g., Serine, Glycine, Glutamic or Aspartic Acid) designed to form a predominantly hydrophilic or predominantly hydrophobic fusion partner for a FGF23 c-tail protein; a functional or non-functional antibody, or a heavy or light chain thereof; and a polypeptide which has an activity, such as a therapeutic activity, different from the FGF23 c-tail proteins of the present invention.

FGF23 c-tail fusion proteins can be made by fusing heterologous sequences at either the N-terminus or at the C-terminus of an FGF 23 c-tail protein. As described herein, a heterologous sequence can be an amino acid sequence or a non-amino acid-containing polymer. Heterologous sequences can be fused either directly to the FGF23 c-tail protein either chemically or by recombinant expression from a single polynucleotide or they may be joined via a linker or adapter molecule. A peptidyl linker or adapter molecule can be one or more amino acid residues (or -mers), e.g., 1, 2, 3, 4, 5, 6, 7, 8, or 9 residues (or -mers), preferably from 10 to 50 amino acid residues (or -mers), e.g., 10, 11, 12, 13, 14, 15, 16, 17, 18, 19, 20, 25, 30, 35, 40, 45, or 50 residues (or -mers), and more preferably from 15 to 35 amino acid residues (or -mers). A linker or adapter molecule can also be designed with a cleavage site for a DNA restriction endonuclease or for a protease to allow for the separation of the fused moieties.

a) Linkers

When forming the fusion proteins of the present invention, a linker can, but need not, be employed. The linker can be made up of amino acids linked together by peptide bonds, i.e., a peptidyl linker. In some embodiments of the present invention, the linker is made up of from 1 to 20 or more amino acids linked by peptide bonds, wherein the amino acids are selected from the 20 naturally occurring amino acids. In some embodiments, the amino acids are selected from the amino acids glycine, serine, and glutamate. In some embodiments, suitable linkers include: GSGEGEGSEGSG (SEQ ID NO:10); GGSEGEGSEGGS (SEQ ID NO:11); and GGGS (SEQ ID NO:12). While a linker of 5 amino acid residues has been found to work with the FGF23 c-tail fusion proteins disclosed herein, the present invention contemplates linkers of any length or composition. Exemplary linkers are shown in Table 2.

TABLE 2

Linker Sequences

| Description | Sequence | SEQ ID NO: |
|---|---|---|
| Linker L1 | GSGEGEGSEGSG | 10 |
| Linker L2 | GGSEGEGSEGGS | 11 |
| Linker L3 | GGGGS | 12 |

The linkers described herein are exemplary, and linkers that are much longer and which include other residues are contemplated by the present invention.

b) Fc Proteins

In some embodiments of the present invention, the FGF23 c-tail proteins are fused to an Fc domain, e.g., one or more domains of an Fc region of a human IgG. Antibodies comprise two functionally independent parts, a variable domain known as "Fab," that binds an antigen, and a constant domain known as "Fc," that is involved in, among other things, effector functions such as complement activation and attack by phagocytic cells. An Fc has a long serum half-life (Capon et al., 1989, Nature 337: 525-31) such that when joined together with a therapeutic protein, an Fc domain can provide longer half-life or incorporate such effector functions as Fc receptor binding, protein A binding, complement fixation, and other characteristics that are desirable in a therapeutic protein.

In vivo pharmacokinetic analysis indicated that wild type human FGF23 c-tail protein has a short half-life. Therefore, to extend the half-life of FGF23 c-tail, Fc sequences were fused to the FGF23 c-tail proteins disclosed herein. Table 3 below illustrates some of the Fc modifications exemplified in this application, and Table 4 below illustrates some of the FGF23 c-tail Fc fusion protein constructs.

TABLE 3

Human IgG1 Fc Sequences

| Description | Amino Acid Sequence | SEQ ID NO: |
|---|---|---|
| Human Wild Type IgG1 Fc (Bold and underlined residues are modified in construct below) | EPKSCDKTHTCPPCPAPELLGGPSVFLEPPKP KDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQP REPQVYTLPPSREEMTKNQVSLTCLVKGFYPS DIAVEWESNGQPENNYKTTPPVLDSDGSFFLY SKLTVDKSRWQQGNVFSCSVMHEALHNHYTQK SLSLSPGK | 13 |
| Human IgG1 FC1 | EPKSCDKTHTCPPCPAPEAAGAPSVFLFPPKP KDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQP REPQVYTLPPSREEMTKNQVSLTCLVKGFYPS DIAVEWESNGQPENNYKTTPPVLDSDGSFFLY SKLTVDKSRWQQGNVFSCSVLHEALHSHYTQK SLSLSPGK | 14 |

TABLE 4

FGF 23 c-tail Fc Fusion Proteins

| Description | Amino Acid Sequence | SEQ ID NO: |
|---|---|---|
| Human Wild Type FGF23 c-tail Fc FGF23-c-tail-FC1 (Linker is underlined and italicized in these constructs) | EPKSCDKTHTCPPCPAPEAAGAPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP G_GGGGS_SAEDDSERDPLNVLKPRARMTPAPASCSQELPSAEDNSPM ASDPLGVVRGGRVNTHAGGTGPEGCRPFAKFI | 15 |
| Human FGF23 c-tail 70 Fc FGF23-c-tail70aa-FC1 (-2 amino acid construct, linker is underlined and italicized in these constructs) | EPKSCDKTHTCPPCPAPEAAGAPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP G_GGGGS_SAEDDSERDPLNVLKPRARMTPAPASCSQELPSAEDNSPM ASDPLGVVRGGRVNTHAGGTGPEGCRPFAK | 16 |
| Human FGF23 c-tail 69 Fc FGF23-c-tail69aa-FC1 (-3 amino acid construct, linker is underlined and italicized in these constructs) | EPKSCDKTHTCPPCPAPEAAGAPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP G_GGGGS_SAEDDSERDPLNVLKPRARMTPAPASCSQELPSAEDNSPM ASDPLGVVRGGRVNTHAGGTGPEGCRPFA | 17 |
| Human FGF 23 c-tail Fc 67 Fc FGF23-c-tail67aa-FC1 (-5 amino acid construct, linker is underlined and italicized in these constructs) | EPKSCDKTHTCPPCPAPEAAGAPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP G_GGGGS_SAEDDSERDPLNVLKPRARMTPAPASCSQELPSAEDNSPM ASDPLGVVRGGRVNTHAGGTGPEGCRP | 18 |

TABLE 4 -continued

FGF 23 c-tail Fc Fusion Proteins

| Description | Amino Acid Sequence | SEQ ID NO: |
|---|---|---|
| Human FGF 23 c-tail 71 + G Fc FGF23-c-tail71 + G-FC1 (71 amino acid + G construct, linker is underlined and italicized in these constructs) | EPKSCDKTHTCPPCPAPEAAGAPSVFLEPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP G*GGGGS*SAEDDSERDPLNVLKPRARMTPAPASCSQELPSAEDNSPM ASDPLGVVRGGRVNTHAGGTGPEGCRPFAKFG | 19 |
| Human FGF 23 c-tail 72 + G Fc FGF23-c-tail72 + G-FC1 (72 amino acid + G construct, linker is underlined and italicized in these constructs) | EPKSCDKTHTCPPCPAPEAAGAPSVFLEPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP G*GGGGS*SAEDDSERDPLNVLKPRARMTPAPASCSQELPSAEDNSPM ASDPLGVVRGGRVNTHAGGTGPEGCRPFAKFIG | 20 |
| Wild Type Murine FGF23 c-tail muFGF23-c-tail-FC1 (linker is underlined and italicized in these constructs) | VPRDAGCKPCICTVPPVSSVFIPPPKPKDVLTITLTPKVTCVVVDI SKDDPEVQFSWFVDDVEVHTAQTQPREEQFNSTFRSVSELPIMHQD WLNGKAFACAVNSAAFPAPIEKTISKTKGRPKAPQVYTIPPPKEQM AKDKVSLTCMITDFFPEDITVEWQWNGQPAENYKNTQPIMDTDGSY FVYSKLNVQKSNWEAGNTPFTCSVLHEGLHNHHTEKSLSHSPG*GGGG* *S*SAEDPPERDPLNVLKPRPRATPVPVSCSRELPSAEEGGPAASDPL GVLRRGRGDARGGAGGADRCRPFPRFV | 21 |

The resulting FGF23 c-tail Fc fusion protein can be purified, for example, by the use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region can be a naturally occurring Fc region, such as an IgG1, IgG2, IgG3 or IgG4 Fc. In one example, an Fc region is a human IgG1 Fc, e.g., SEQ ID NO:13. The Fc region can also be altered to improve certain qualities, such as modification to reduce effector function, e.g. SEQ ID NO:14, or modified to improve therapeutic qualities, such as increased circulation time (half-life).

c) Effects on Serum Phosphate and 1,25VitD

The FGF23 fusion proteins of the present invention modulate serum phosphate levels without substantially changing or leading to a change in serum 1,25VitD levels.

Binding of FGF23 to FGFR1c, FGFR3c, and FGFR4/α-klotho receptor complexes actively modulates both phosphate and 1,25D via activation of signaling pathways. In co-immunoprecipitation experiments, it was shown that the FGF23 c-tail peptide can effectively compete with full-length FGF23 for binding to each of the three cognate FGFR/aKlotho complexes of FGF23 (Goetz et al., (2010) Proc Natl Acad Sci USA 107:407-412). This is consistent with the FGF23 c-tail region mediating binding of FGF23 to cognate FGFR/αKlotho complexes. One possible explanation for the differential modulation of serum phosphate and 1,25VitD by the FGF23 c-tail Fc might be that the fusion molecule has different binding affinities for the cognate FGFR/aKlotho complexes of FGF23. As the binding contacts of FGF23 and the FGF23 c-tail to the various receptor complexes have not been defined to date, we speculate that fusion of the FGF23 c-tail to the Fc might preclude binding to specific receptor complexes, and perhaps steric hindrance could be responsible for differential receptor binding.

In one embodiment, the FGF23 c-tail protein is fused to a heterologous protein comprising a dimerization domain. In another embodiment, the FGF23 c-tail Fc fusion proteins of the present invention modulate serum phosphate levels without substantially modulating serum 1,25VitD levels as compared to a monomeric FGF23 c-tail protein or a FGF23 c-tail Fc fusion protein which does not form a dimer.

In another embodiment, the fusion of the FGF23 c-tail peptide to a heterologous protein results in the anchoring of two FGF23 c-tail peptide domains in close proximity to one another.

An increased serum calcium-phosphate product may result in soft tissue mineralization, a potentially serious and irreversible condition. 1,25 VitD promotes the reabsorption of both phosphate and calcium in the gut. Therefore, increased 1,25 VitD levels might promote an increased calcium-phosphate product and potentially increase the risk for soft-tissue mineralization. Modulation of serum phosphate levels without substantially modulating serum 1,25VitD levels might bear less risk for soft tissue mineralization than treatments, which lead to marked increases in serum 1,25VitD.

Pharmaceutical Compositions

Pharmaceutical compositions comprising FGF23 c-tail fusion proteins are within the scope of the present invention, and are specifically contemplated in light of the identification of several fusion proteins exhibiting enhanced properties. Such pharmaceutical compositions can comprise a therapeutically effective amount of a FGF23 c-tail fusion protein, in admixture with a pharmaceutically or physiologically acceptable formulation agent selected for suitability with the mode of administration. Acceptable formulation agents preferably are nontoxic to recipients at the dosages and concentrations employed.

The pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition. Suitable formulation agents include, but are not limited to, amino acids (such as glycine, glutamine, asparagine, arginine, or lysine), antimicrobials, antioxidants (such as ascorbic acid, sodium sulfite, methionine or sodium hydrogen-sulfite), buffers (such as borate, bicarbonate, Tris-HCl, histidine, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., Remington's Pharmaceutical Sciences (18th Ed., A.R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., Remington's Pharmaceutical Sciences, supra). Such compositions can influence the physical state, stability, rate of in vivo release, and rate of in vivo clearance of the FGF23 c-tail fusion protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Histidine or Tris buffer of about pH 6.0-8.5, which can further include sorbitol or a suitable substitute. In one embodiment of the present invention, FGF23 c-tail fusion protein compositions can be prepared for storage by mixing the selected composition having the desired degree of purity with optional formulation agents (Remington's Pharmaceutical Sciences, supra) in the form of a an aqueous solution.

The pharmaceutical compositions can be selected for parenteral delivery. Alternatively, the compositions can be selected for inhalation or for delivery through the digestive tract, such as orally. The preparation of such pharmaceutically acceptable compositions is within the skill of the art. The formulation components are present in concentrations that are acceptable to the site of administration. For example, buffers are used to maintain the composition at physiological pH or at a slightly lower pH, typically within a pH range of from about 6 to about 8.

When parenteral administration is contemplated, the therapeutic compositions for use in this invention can be in the form of a pyrogen-free, parenterally acceptable, aqueous solution comprising the desired FGF23 c-tail fusion protein, in a pharmaceutically acceptable vehicle. A particularly suitable vehicle for parenteral injection is sterile distilled water in which a FGF23 c-tail fusion protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, the pharmaceutical composition can be formulated as a dry powder for inhalation. Inhalation solutions can also be formulated with a propellant for aerosol delivery. In yet another embodiment, solutions can be nebulized. Pulmonary administration is further described in International Publication No. WO94/20069, which describes the pulmonary delivery of chemically modified proteins.

It is also contemplated that certain formulations can be administered orally. In one embodiment of the present invention, formulations that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption. Diluents, flavorings, low melting point waxes, vegetable oils, lubricants, suspending agents, tablet disintegrating agents, and binders can also be employed.

Another pharmaceutical composition can involve an effective quantity of FGF 23 c-tail fusion protein in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving FGF23 c-tail fusion proteins, in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO93/15722, which describes the controlled release of porous polymeric microparticles for the delivery of pharmaceutical compositions, and Wischke & Schwendeman, 2008, Int. J. Pharm. 364: 298-327, and Freiberg & Zhu, 2004, Int. J. Pharm. 282: 1-18, which discuss microsphere/microparticle preparation and use). As described herein, a hydrogel is an example of a sustained- or controlled-delivery formulation.

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et ah, 1983, Biopolymers 22: 547-56), poly(2-hydroxyethyl-methacrylate) (Langer et ah, 1981, J. Biomed. Mater. Res. 15: 167-277 and Langer, 1982, Chem. Tech. 12: 98-105), ethylene vinyl acetate (Langer et al, supra) or poly-D(–)-3-hydroxybutyric acid (European Patent No. 0 133 988). Sustained-release compositions can also include liposomes, which can be prepared by any of several methods known in the art. See, e.g., Epstein et ah, 1985, Proc. Natl. Acad. Sci. U.S.A. 82: 3688-92; and European Patent Nos. 0 036 676, 0 088 046, and 0 143 949.

The pharmaceutical composition to be used for in vivo administration typically should be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle. The parenteral composition can be diluted into parenteral acceptable diluents (e.g., saline and 5% Dextrose).

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In one embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and dual chamber syringes).

In one embodiment, the present invention is directed to a pharmaceutical composition comprising a FGF23 c-tail fusion protein formulated as a powder for injection after reconstitution to a solution for injection.

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, Fc fusion therapeutic proteins, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343: 1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., increased serum phosphate or decreased phosphate excretion.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising the FGF23 c-tail fusion proteins of the disclosure can be provided by continuous infusion, or by doses at intervals of, e.g., one day, one week, 1-7 times per week, or one month. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, New Engl. J. Med. 349:427-434; Herold, et al., 2002, New Engl. J. Med. 346:1692-1698; Liu, et al., 1999, J. Neurol. Neurosurg. Psych. 67:451-456; Portielji, et al., 2003, Cancer. Immunol. Immunother. 52: 133-144). The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For therapeutic FGF23 c-tail fusion proteins of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the therapeutic protein of the disclosure may be calculated using the patient's weight in kilograms (kg) multiplied by the dose to be administered in mg/kg. The dosage of the proteins of the disclosure may be 150 µg/kg or less, 125 µg/kg or less, 100 µg/kg or less, 95 µg/kg or less, 90 µg/kg or less, 85 µ/kg or less, 80 µ/kg or less, 75 µ/kg or less, 70 µ/kg or less, 65 µ/kg or less, 60 µ/kg or less, 55 µ/kg or less, 50 µ/kg or less, 45 µ/kg or less, 40 µ/kg or less, 35 µ/kg or less, 30 µ/kg or less, 25 µ/kg or less, 20 µ/kg or less, 15 µ/kg or less, 10 µ/kg or less, 5 µ/kg or less, 2.5 µ/kg or less, 2 µ/kg or less, 1.5 µ/kg or less, 1 µ/kg or less, 0.5 µ/kg or less, or 0.1 µ/kg or less of a patient's body weight.

Unit dose of the therapeutic proteins of the disclosure may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the therapeutic proteins of the disclosure may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 v, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml/ml, or at least 400 µg/ml/ml in a subject. Alternatively, the dosage of the antibodies of the disclosure may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of therapeutic proteins of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an engineered antibody or engineered antibody conjugate, combination therapy, or a composition of the disclosure is administered using Alkermes AIR™ pulmonary drug delivery technology (Alkermes, Inc., Cambridge, Mass.).

The frequency of dosing will depend upon the pharmacokinetic parameters of the FGF23 c-tail fusion protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by subcutaneous, intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration. In order to deliver drug, e.g., a FGF23 c-tail fusion protein as disclosed herein, at a predetermined rate such that the drug concentration can be maintained at a desired therapeutically effective level over an extended period, a variety of different approaches can be employed. In one example, a hydrogel comprising a polymer such as a gelatin (e.g., bovine gelatin, human gelatin, or gelatin from another source) or a naturally-occurring or a synthetically generated polymer can be employed. Any percentage of polymer (e.g., gelatin) can be employed in a hydrogel, such as 5, 10, 15 or 20%. The selection of an appropriate concentration can depend on a variety of factors, such as the therapeutic profile desired and the pharmacokinetic profile of the therapeutic molecule.

Examples of polymers that can be incorporated into a hydrogel include polyethylene glycol ("PEG"), polyethylene oxide, polyethylene oxide-co-polypropylene oxide, co-polyethylene oxide block or random copolymers, polyvinyl alcohol, poly(vinyl pyrrolidinone), poly(amino acids), dextran, heparin, polysaccharides, polyethers and the like.

Another factor that can be considered when generating a hydrogel formulation is the degree of crosslinking in the hydrogel and the crosslinking agent. In one embodiment, cross-linking can be achieved via a methacrylation reaction involving methacrylic anhydride. In some situations, a high degree of cross-linking may be desirable while in other situations a lower degree of crosslinking is preferred. In some cases a higher degree of crosslinking provides a longer sustained release. A higher degree of crosslinking may provide a firmer hydrogel and a longer period over which drug is delivered. Any ratio of polymer to crosslinking agent (e.g., methacrylic anhydride) can be employed to generate a hydrogel with desired properties. For example, the ratio of polymer to crosslinker can be, e.g., 8:1, 16:1, 24:1, or 32:1. For example, when the hydrogel polymer is gelatin and the crosslinker is methacrylate, ratios of 8:1, 16:1, 24:1, or 32:1 methyacrylic anhydride:gelatin can be employed.

Methods of Treatment

FGF23 c-tail fusion proteins and pharmaceutical compositions comprising the FGF23 c-tail fusion proteins can be used to regulate FGF23-mediated or FGF receptor (FGFR)/α-klotho complex-mediated regulation of mineral ions, such as phosphate and calcium, and 1,25 VitD. Accordingly, the proteins of the invention can be used to inhibit the activity of FGF23 and, thus, can be used to treat a variety of diseases or disorders mediated by interaction of FGF23 with an FGF receptor (FGFR)/α-klotho complex. In addition, the invention provides for use of the FGF23 c-tail fusion proteins, or pharmaceutical compositions thereof, of this disclosure in the manufacture of a medicament for use in treatment or prevention of FGF23 mediated or FGF receptor (FGFR)/α-klotho complex-mediated disorders. In another embodiment, the invention provides for use of the FGF23 c-tail fusion proteins, or pharmaceutical compositions thereof, of this disclosure in the manufacture of a medicament for use in treatment or prevention of FGF23-mediated mediated disorders that are independent of α-klotho or use an alternate co-receptor. Examples of FGF23 mediated or FGF receptor (FGFR)/α-klotho complex-mediated disorders that can be treated include, but are not limited to, autosomal dominant hypophosphatemic rickets (ADHR), X-linked hypophosphatemic rickets (XLH), tumor-induced osteomalacia (TIO), fibrous dysplasia (FD), and chronic kidney disease (CKD).

The proteins of the invention, or pharmaceutical compositions thereof, may also be used in methods of treating diseases or disorders including left ventricular hypertrophy and hyperparathyroidism. The invention also provides for use of the FGF23 c-tail fusion proteins, or pharmaceutical compositions thereof, of this disclosure in the manufacture of a medicament for use in treatment or prevention of diseases or disorders including left ventricular hypertrophy and hyperparathyroidism.

The FGF23 c-tail fusion proteins of the present invention may be used therapeutically in hypophosphatemic conditions where FGF23 is not the primary cause of hypophosphatemia, and is not down-regulated as a compensatory mechanism, because they enhance renal phosphate retention. Hypophosphatemic conditions which may be treated by the fusion proteins of the present invention include, among others, refeeding syndrome, diabetic ketoacidosis, asthma exacerbations and chronic obstructive pulmonary disease, and recovery from organ (particularly, kidney) transplantation (Gaasbeek et al., "Hypophosphatemia: An Update on its Etiology and Treatment," *Am J Med* 118(10):1094-1101 (2005); Miller et al., "Hypophosphatemia in the Emergency Department Therapeutics," *Am J Emerg Med* 18(4):457-461 (2000); Marinella M A., "Refeeding Syndrome and Hypophosphatemia,"*J Intensive Care Med* 20(3)155-159 (2005). In application, a disorder or condition mediated by the interaction between FGF23 and an FGF receptor (FGFR)/α-klotho complex can be treated by administering an FGF23 c-tail fusion protein, or a pharmaceutical composition thereof, as described herein, to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of an FGF23 c-tail fusion protein. It will be apparent to those of skill in the art that a therapeutically effective dose will depend, inter alia, upon the administration schedule, the unit dose of agent administered, whether the composition is administered in combination with other therapeutic agents, and the health of the recipient. The term "therapeutically effective dose," as used herein, means that amount of FGF23 c-tail fusion protein that elicits the biological or medicinal response in a tissue system, animal, or human being sought by a researcher, medical doctor, or other clinician, which includes alleviation of the symptoms of the disease or disorder being treated.

Exemplary Embodiments

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1: Cloning and Expression of the Fc-FGF23 Fusion Protein

This example illustrates the generation and expression of the Fc-FGF23 fusion proteins described herein.

The human Fc-FGF23 fusion protein coding sequence was designed to contain a leader peptide, the hinge of a Human IgG1, a mutated effectorless variant CH2-CH3 region of a human IgG1, a single GGGGS linker, followed by the C-terminal 72 amino acids of human wild type FGF23 and is shown in Table 5. The predicted amino acid sequence of the pre-Fc-FGF23 fusion protein, and the mature secreted product are shown in Table 5 respectively.

As one of the desired properties of FGF23 c-tail Fc fusion proteins is to competitively inhibit the binding of FGF23 to the FGF23 receptor/α-klotho coreceptor complex, native Fc functions such as antibody-dependent cell-mediated cytotoxicity (ADCC) and complement-dependent cytotoxicity (CDC) are generally not preferred. Using a set of mutations as described by Winter et al. in U.S. Pat. Nos. 5,624,821 and 5,648,260, effector functions were engineered out of human IgG1 Fc by mutating the positions Leu242, Leu243 and Gly245 to alanines (234, 235 and 237, respectively, per Kabat antibody numbering (see Tables 4 and 5)). These mutations from LLGL to AAGA are expected to reduce Fc effector functions including Fc mediated cell depletion. See, e.g., U.S. Pat. Nos. 5,624,821 and 5,648,260.

The sequence was constructed as a syngene by a commercial vendor (Genewiz, South Plainfield N.J.) and recloned into a proprietary mammalian expression vector. This construct was transfected into a proprietary CHO cell line and a stable pool of transfectants was selected. After selection, the transfected pool was scaled to 1 L at an initial density of 1E6/ml and a production run was initiated. Use of a daily feed schedule enabled production runs of 14-16 days, with typical fusion protein titers of 6-900 mg/L. The supernatants were harvested by centrifugation and sterile filtered before purification.

TABLE 5

Human FGF 23 c-tail Fc Fusion Protein Constructs

| Description | Amino Acid Sequence | SEQ ID NO: |
|---|---|---|
| Human Wild Type FGF23 c-tail Fc coding sequence | atgggatggagctgtatcatcctcttcttggtggcaacagctacag gcgtgcactccgagcccaaatcttgtgacaaaactcacacatgccc accgtgcccagcacctgaagccgctggggcaccgtcagtcttcctc ttccccccaaaacccaaggacaccctcatgatctcccggacccctg aggtcacatgcgtggtggtggacgtgagccacgaagaccctgaggt caagttcaactggtacgtggacggcgtggaggtgcataatgccaag acaaagccgcgggaggagcagtacaacagcacgtaccgtgtggtca gcgtcctcaccgtcctgcaccaggactggctgaatggcaaggagta caagtgcaaggtctccaacaaagcccctcccagcccccatcgagaaa accatctccaaagccaaagggcagccccgagaaccacaggtgtaca ccctgcccccatcccgggaggagatgaccaagaaccaggtcagcct gacctgcctggtcaaaggcttctatcccagcgacatcgccgtggag tgggagagcaatgggcagccggagaacaactacaagaccacgcctc ccgtgctggactccgacggctccttcttcctctatagcaagctcac cgtggacaagagcaggtggcagcaggggaacgtcttctcatgctcc gtgatgcatgaggctctgcacaaccactacacgcagaagagcctct ccctgtcccggggtggcggaggggggcagcagcgccgaggacgactc ggagcgggacccctgaacgtgctgaagcccgggccggatgacc ccggccccggcctcctgttcacaggagctcccgagcgccgaggaca acagcccgatggccagtgacccattaggggtggtcaggggcggtcg agtgaacacgcacgctgggggaacgggcccggaaggctgccgcccc ttcgccaagttcatctga | 22 |
| Human Wild Type FGF23 C-Tail Fc Precursor Amino Acid Sequence (effector function mutations in bold and underlined) | MGWSCIILFLVATATGVHSEPKSCDKTHTCPPCPAPEAAGAPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSREEMTKNQVSLTCLVKGFYPSDIAVE WESNGQPENNYKTTPPVLDSDGSFFLYSKLTVDKSRWQQGNVFSCS VMHEALHNHYTQKSLSLSPGGGGGSSAEDDSERDPLNVLKPRARMT PAPASCSQELPSAEDNSPMASDPLGVVRGGRVNTHAGGTGPEGCRP FAKFI | 23 |
| Human Wild Type FGF23 C-Tail Fc Mature Amino Acid Sequence (effector function mutations in bold and underlined) | EPKSCDKTHTCPPCPAPEAAGAPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP GGGGGSSAEDDSERDPLNVLKPRARMTPAPASCSQELPSAEDNSPM ASDPLGVVRGGRVNTHAGGTGPEGCRPFAKFI | 15 |

The murine orthologue was designed in a manner analogous to the human Fc fusion. The syngene consisted of the same leader peptide sequence as the human, followed by a murine IgG1 hinge, effectorless murine FC, a GGGGS linker, followed by the carboxyl-terminal 72 amino acids of murine FGF23. The DNA sequence of the coding region, the predicted amino acid sequence of the pre-Fc-FGF23 protein, and the predicted mature product are shown in Table 6. The syngene was synthesized by Genewiz (Genewiz, South Plainfield N.J.) as per the human construct, and subcloned into the same proprietary vector backbone as the human. It was later determined that there were product quality issues with the materials produced in CHO cells, and the surrogate mouse fusion protein was produced by large scale transient transfections using the human embryonic kidney cell line HEK293 using the FreeStyle 293 family of cells, reagents and media (Life Technologies, Grand Island N.Y.) as per manufacturers' protocols.

TABLE 6

Murine FGF 23 c-tail Fc Fusion Protein Constructs

| Description | Amino Acid Sequence | SEQ ID NO: |
|---|---|---|
| Murine Wild Type FGF23 c-tail Fc coding sequence | atgggatggagctgtatcatcctcttcttggtggcaacagctacaggcgtgca ctccgtgcccagggatgccggttgtaagccttgcatatgtacagtcccaccag tatcatctgtcttcatcttccccccaaagcccaaggatgtgctcaccattact ctgactcctaaggtcacgtgtgttgtggagacatcagcaaggatgatcccga ggtccagttcagctggtttgtagatgatgtggaggtgcacacagctcagacgc aacccggggaggagcagttcaacagcactttccgctcagtcagtgaacttccc atcatgcaccaggactggctcaatggcaaggccttcgcatgcgcggtcaacag tgcagctttccctgcccccatcgagaaaaccatctccaaaaccaaaggcagac cgaaggctccacaggtgtacaccattccacctcccaaggagcagatggccaag gataaagtcagtctgacctgcatgataacagacttcttccctgaagacattac tgtggagtggcagtggaatgggcagccagcggagaactacaagaacactcagc ccatcatggacacagatggctcttacttcgtctacagcaagctcaatgtgcag | 24 |

TABLE 6 -continued

Murine FGF 23 c-tail Fc Fusion Protein Constructs

| Description | Amino Acid Sequence | SEQ ID NO: |
|---|---|---|
| | aagagcaactgggaggcaggaaatactttcacctgctctgtgttacatgaggg<br>cctgcacaaccaccatactgagaagagcctctcccactctcctggtggcggag<br>ggggcagcagcgccgaggacccacccgagcgcgacccactgaacgtgctcaag<br>ccgcggccccgcgccacgcctgtgcctgtatcctgctctcgcgagctgccgag<br>cgcagaggaaggtggccccgcagccagcgatcctctgggggtgctgcgcagag<br>gccgtggagatgctcgcggggcgcgggaggcgcggataggtgtcgcccctttc<br>ccaggttcgtctag | |
| Murine Wild Type FGF23 C-Tail Fc Precursor Amino Acid Sequence | MGWSCIILFLVATATGVHSVPRDAGCKPCICTVPPVSSVFIFPPKP<br>KDVLTITLTPKVTCVVVDISKDDPEVQFSWFVDDVEVHTAQTQPRE<br>EQFNSTFRSVSELPIMHQDWLNGKAFACAVNSAAFPAPIEKTISKT<br>KGRPKAPQVYTIPPPKEQMAKDKVSLTCMITDFFPEDITVEWQWNG<br>QPAENYKNTQPIMDTDGSYFVYSKLNVQKSNWEAGNTFTCSVLHEG<br>LHNHHTEKSLSHSPGGGGGSSAEDPPERDPLNVLKPRPRATPVPVS<br>CSRELPSAEEGGPAASDPLGVLRRGRGDARGGAGGADRCRPFPRFV | 25 |
| Murine Wild Type FGF23 C-Tail Fc Mature Amino Acid Sequence | VPRDAGCKPCICTVPPVSSVFIFPPKPKDVLTITLTPKVTCVVVDI<br>SKDDPEVQFSWFVDDVEVHTAQTQPREEQFNSTFRSVSELPIMHQD<br>WLNGKAFACAVNSAAFPAPIEKTISKTKGRPKAPQVYTIPPPKEQM<br>AKDKVSLTCMITDFFPEDITVEWQWNGQPAENYKNTQPIMDTDGSY<br>FVYSKLNVQKSNWEAGNTFTCSVLHEGLHNHHTEKSLSHSPGGGGG<br>SSAEDPPERDPLNVLKPRPRATPVPVSCSRELPSAEEGGPAASDPL<br>GVLRRGRGDARGGAGGADRCRPFPRFV | 21 |

Example 2: C-Terminal Fusion of FGF23 c-Tail Peptides to IgG1 Fc

Various PEG moieties conjugated to the FGF23 c-tail peptide on either the C-terminus or the N-terminus abolished or significantly reduced the peptide's inhibitory activity, making PEGylation a non-viable option. In contrast, fusion of the FGF23 c-tail peptide to an effectorless human Fc did not significantly impact the peptide's inhibitory activity. Interestingly, in an SPR-based competitive binding assay, the more untraditional C-terminal fusion showed greater inhibitory potency than the N-terminal fusion (FIG. 1). Additionally, while titers of the C-terminal and N-terminal Fc fusions were similar, purification yield was significantly higher for the C-terminal fusion.

Example 3: Purification and Characterization of Fc-FGF23 c-tail Fusion Proteins This example illustrates the purification and characterization of the fusion proteins obtained from the experiment described in Example 1 above.

Human FGF23-Fc was purified by Protein A affinity (MabSelect SuRe, GE Healthcare, Pittsburgh Pa., 17-5438) and ceramic hydroxyapatite (Macroprep CHT Type II, 40 µm, BioRad Hercules Calif., 157-4000) chromatography. Preliminary formulation studies were performed at 5 mg/ml and 50-65 mg/ml in HBS (20 mM Hepes, 150 mM NaCl, pH 7.5) and TMS buffer (1.2 mg/ml Tris, 40 mg/ml mannitol, 10 mg/ml sucrose, pH 7.5). The material was most stable in TMS buffer when concentrated to 50 mg/ml.

Murine FGF23-Fc was purified by Protein A affinity (MabSelect SuRe, GE Healthcare, 17-5438) and preparative SEC (Superdex 200pg, GE, 28-9893). The final pool was formulated at approximately 5 mg/ml in 20 mM Hepes, 150 mM NaCl, pH 7.5.

All lots of FGF23-Fc were characterized by UV absorbance, SDS-PAGE, Analytical SEC, Intact Mass Spectrometry, and endotoxin.

Figure 2A:
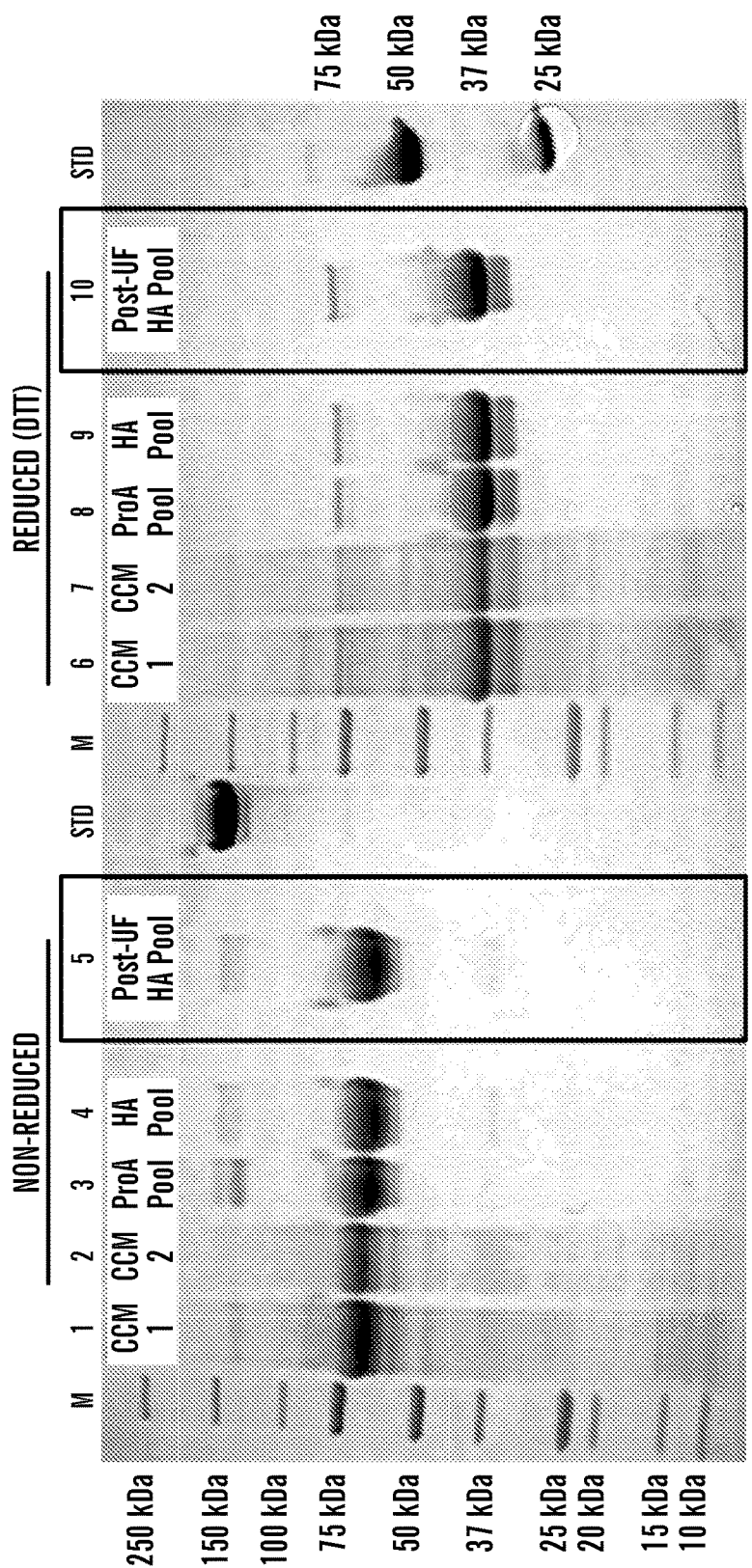
FIG. 2A shows a SDS-Page analysis of FGF23-c-tail-FC1 purification (8 μg load).
Figure 2B:
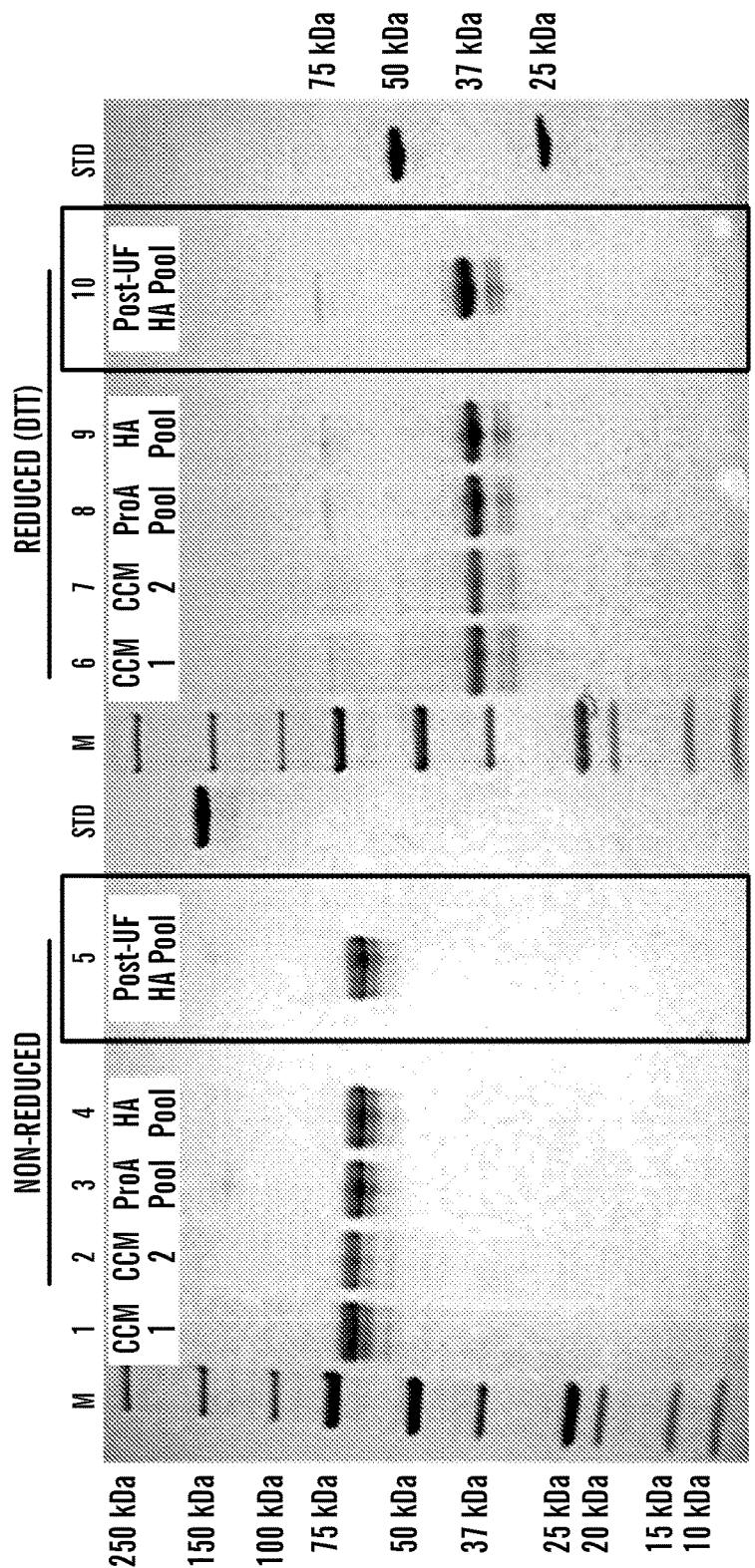
FIG. 2B shows a SDS-Page analysis of FGF23-c-tail-FC1 purification (2 μg load). The SDS PAGE gel presents both non-reduced and reduced conditions and highlights the purity of the material tested as well as the disulfide driven dimer nature of the molecule than can be fully reduced to monomer with dithiothreitol (DTT) treatment in the denaturing condition of this gel.

Absorbances at 280 nm and 320 nm were measured using an Implen Nanophotometer. SDS-Page analysis was performed using tris-glycine gels with 8 and 2 µg protein load under reduced and non-reduced conditions. Gels were run at 200V for 40 minutes and detected with coomassie G250, per manufacturer's recommendations. FIGS. 2A and 2B depict the SDS gels.

Figure 3:
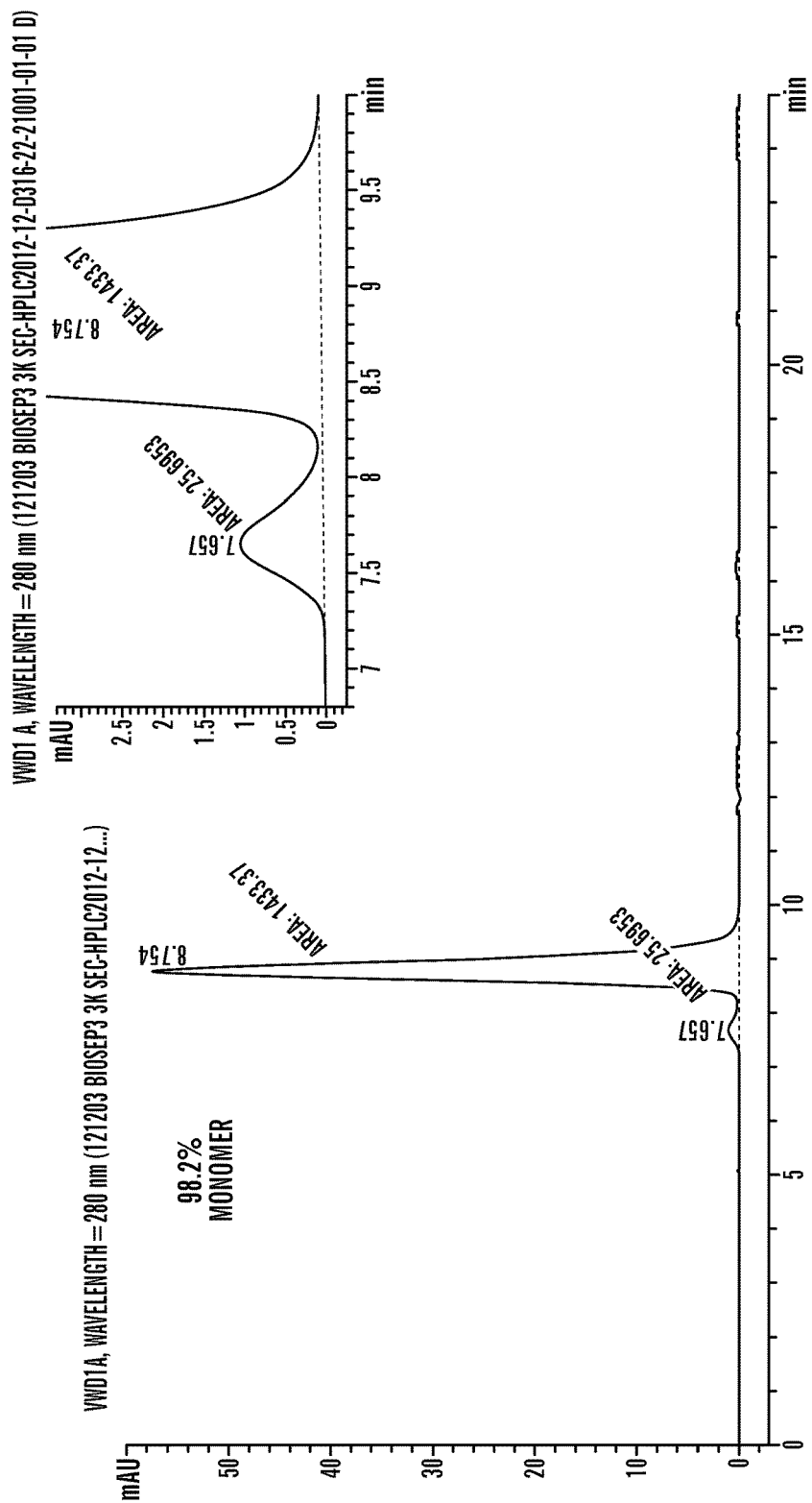
FIG. 3, depicts a graph showing results of an analytical size exclusion chromatography run with the FGF23-c-tail-FC1. Note the low percentage of oligomer species compared to the monomer of FGF23-c-tail-FC1.
Figure 4A:
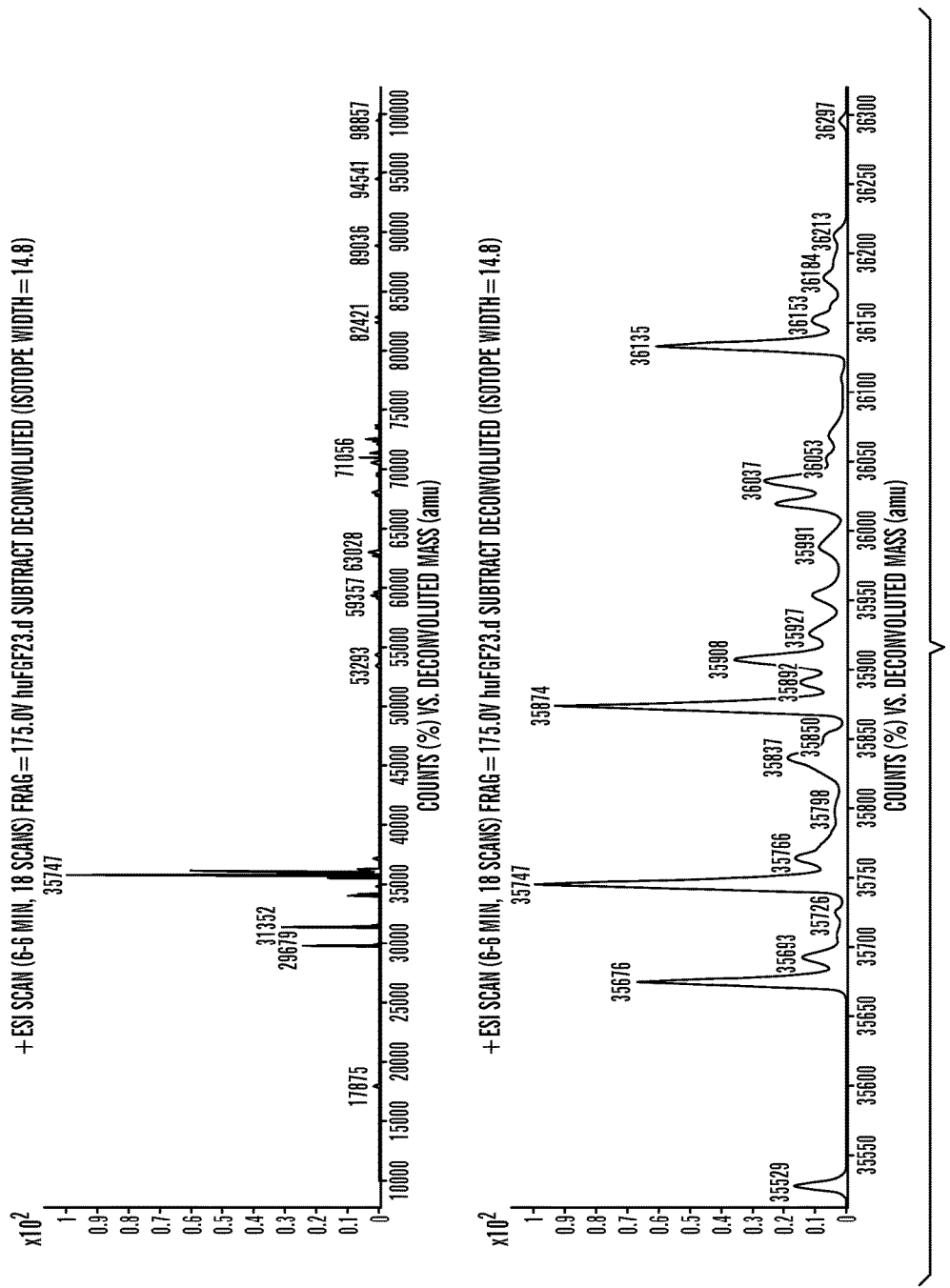
FIG. 4A shows Intact Mass analysis by ESI TOF under reducing conditions.
Figure 4B:
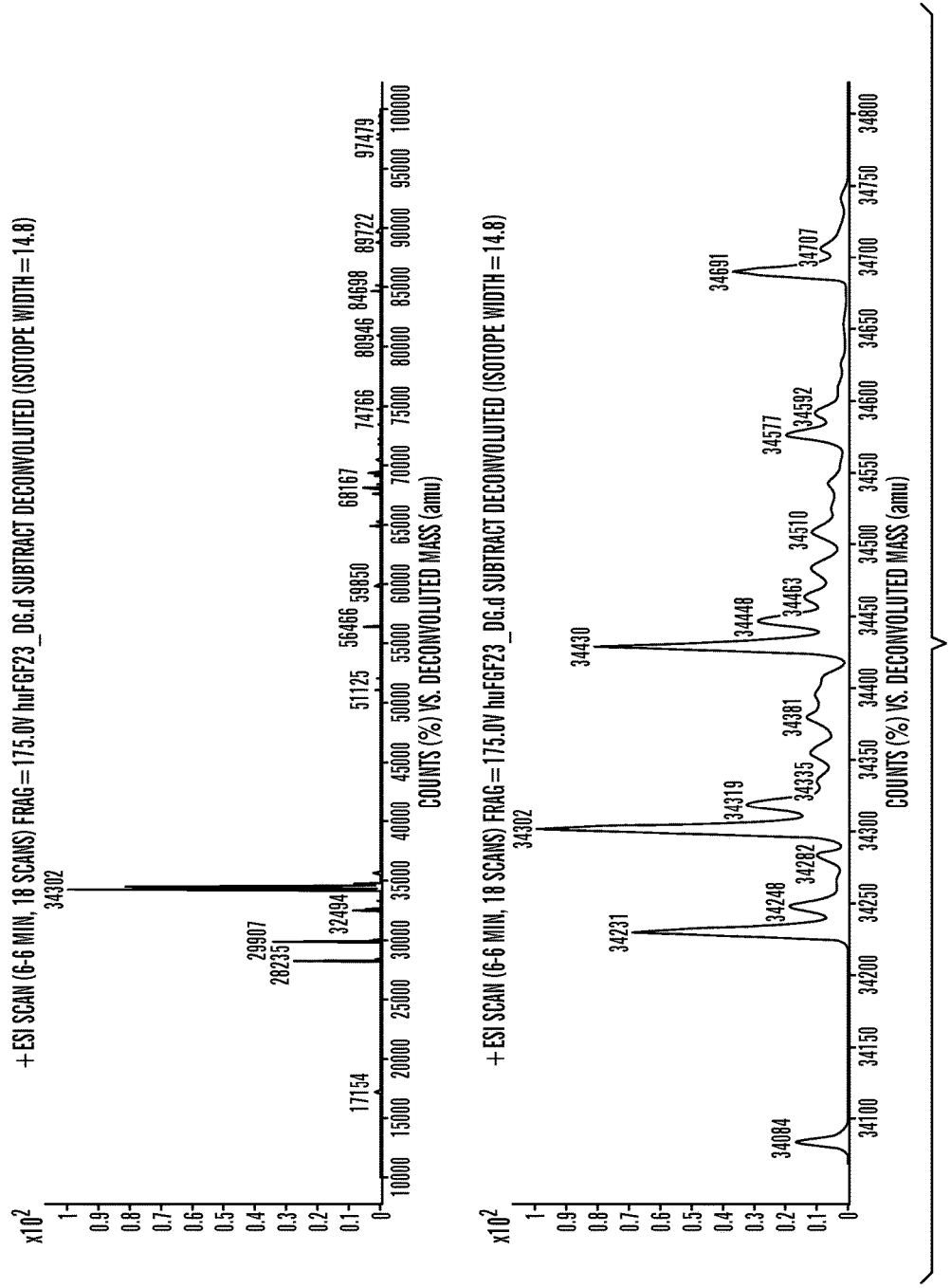
FIG. 4B shows Intact Mass analysis by ESI TOF under reducing conditions and PGNaseF treatment.

FIG. 3 depicts an analytical SEC-HPLC run on a BioSep-SEC-s3000 column (Phenomenex, Part#00H-2146-K0) in a 20 mM phosphate, 400 mM NaCl, pH 7.2 mobile phase. Approximately 25 µg of FGF23-Fc fusion protein were applied to a pre-equilibrated column. The column was run at 1 ml/min for a duration of 25 minutes. FIG. 4 depicts graphs showing, intact mass analysis, which was performed using ESI TOF (Agilent Technologies). Samples were analyzed after reduction and with and without PNGaseF treatment. Endotoxin levels were measured using a portable Endosafe-PTS instrument (Charles River Laboratories, Wilmington Mass.).

Approximately 11 grams of purified HuFGF23-Fc material were produced from 2x~20 L stable CHO wave cultures, reflecting a yield of 57%. The final material (Post-UF HA) was determined to be 98.2% monomer by analytical SEC and 0.2 EU/mg. SDS-Page analysis determined that the final material is ~74% species of interest using this purification process and is consistent with the previous small scale lot. Intact mass analysis showed that the main species after reduction and treatment to remove N-linked glycan are 34231, 34302 Da, and 34430 Da. The differences between the molecular weights found by mass spec analysis and the expected mass of 33,745 Da is likely o-linked glycosylation and minor truncated species. This mass profile is consistent with the previous lots.

Example 4: C-terminal FGF23 c-tail Fc Truncations

Figure 5A:
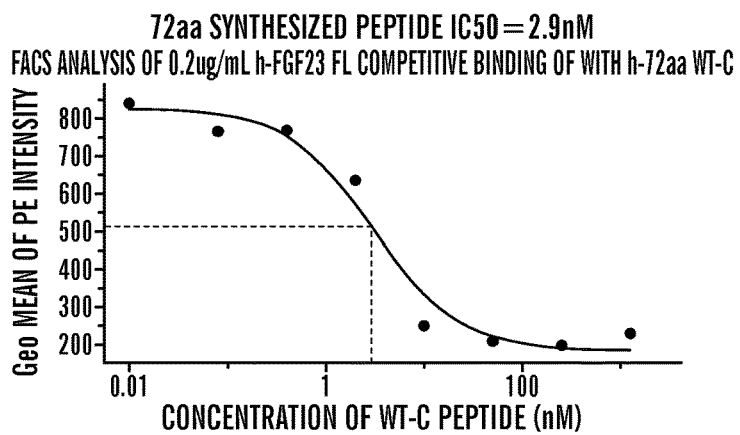
FIG. 5, comprising panels A, B, and C, depicts the competitive binding of the FGF23 c-tail peptide as compared to truncated FGF23 c-tail peptides, 70 amino acids and 69 amino acids in length.
Figure 5B:
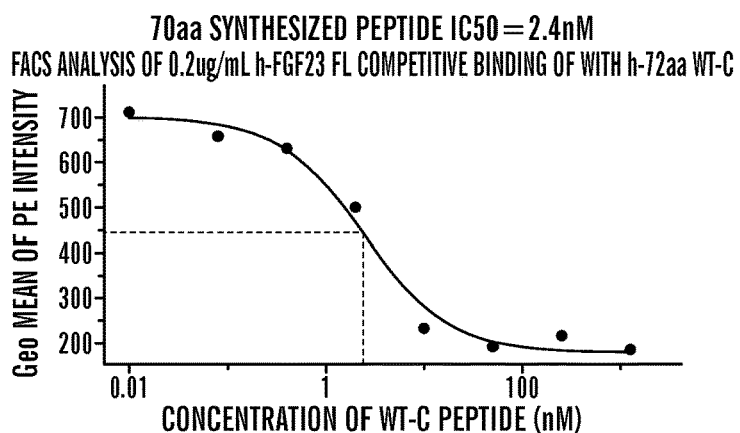
Figure 5C:
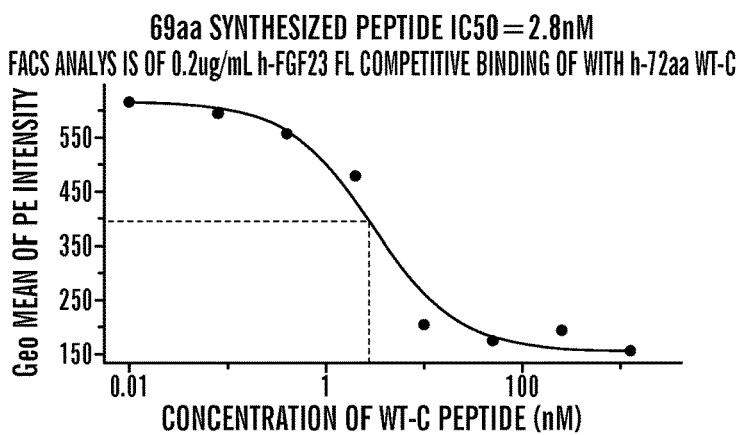

Molecular characterization of both the C-terminal FGF23 c-tail Fc and the N-terminal FGF23 c-tail Fc showed evidence of truncations, though the presence of these truncations was heterogeneous within the sample. The N-terminal truncations were predicted to ablate activity in molecules in which the truncation had occurred. The heterogeneity of truncations for the C-terminal fusion is shown in FIG. 4. To assess whether loss of the first 2-3aa from the C-terminus of the FGF23 c-tail peptide impacts the inhibitory potency of the peptide, competitive binding assays using HEK293 cells engineered to overexpress alpha-klotho were performed. HEK293 cells are human cells embryonic kidney cells that endogenously express several FGFRs (Kurosu et al., (2006) J Biol Chem 281: 6120-6123; Yamazaki et al., (2010) J Cell Biochem 111:1210-1221), including cognate FGFRs of FGF23. Ectopic expression of alpha-klotho in these cells enables potent binding, and signaling, of FGF23 (Kurosu et al., (2006) J Biol Chem 281: 6120-6123). Pre-treatment of HEK293-klotho cells with the 72aa FGF23 c-tail (both in the form of a synthesized peptide and an Fc fusion) inhibits the ability of sub-saturating amounts of FGF23 to bind these cells in a dose responsive manner as assessed by flow cytometry. FGF23 protein (both human and mouse described herein) were produced using a Mouse myeloma cell line (NSO). Synthetic FGF23 c-tail peptides and FGF23 c-tail Fc fusion proteins composed of 72, 70 or 69aa (peptide) or 69 and 67aa (Fc fusion) of the FGF23 c-tail were generated. As shown in FIG. 5, truncation of the FGF23 c-tail peptide component of the FGF23 c-tail Fc fusion by 2-3aa from the C-terminus did not impact competitive binding activity of the fusion protein. Mass spec analysis shows that generation of a 69 or 67aa FGF23 c-tail Fc fusion prohibits additional clipping of the molecule (Table 7). Hence these fusion proteins can also be used as potential therapeutics in the treatment of XLH.

TABLE 7

Mass Spec Analysis of Truncated FGF23 c-tail Fc Fusions

| Truncated Form | Sequence | Intensity | % |
|---|---|---|---|
| Hu FGF23 69aa Fc (−3aa construct) | | | |
| minus 3 AA | VNTHAGGTGPEGCRPFA | 2.44E+08 | 95.9 |
| minus 4 AA | VNTHAGGTGPEGCRPF | 9.66E+06 | 3.8 |
| minus 5 AA | VNTHAGGTGPEGCRP | 2.36E+05 | 0.1 |
| minus 6 AA | VNTHAGGTGPEGCR | 4.30E+05 | 0.2 |
| minus 7 AA | VNTHAGGTGPEGC | 2.49E+04 | 0.0 |
| Hu FGF23 67aa Fc (−5aa construct) | | | |
| minus 5 AA | VNTHAGGTGPEGCRP | 2.14E+08 | 100.0 |
| minus 6 AA | VNTHAGGTGPEGCR | 4.60E+04 | 0.0 |
| minus 7 AA | VNTHAGGTGPEGC | 1.99E+04 | 0.0 |

Example 5: Inhibitory Potency of FGF23 c-tail Fusion Proteins

This example illustrates the inhibitory potency of the Human 72aa FGF23 C-tail Fc fusion in a cell-based assay.

Figure 6A:
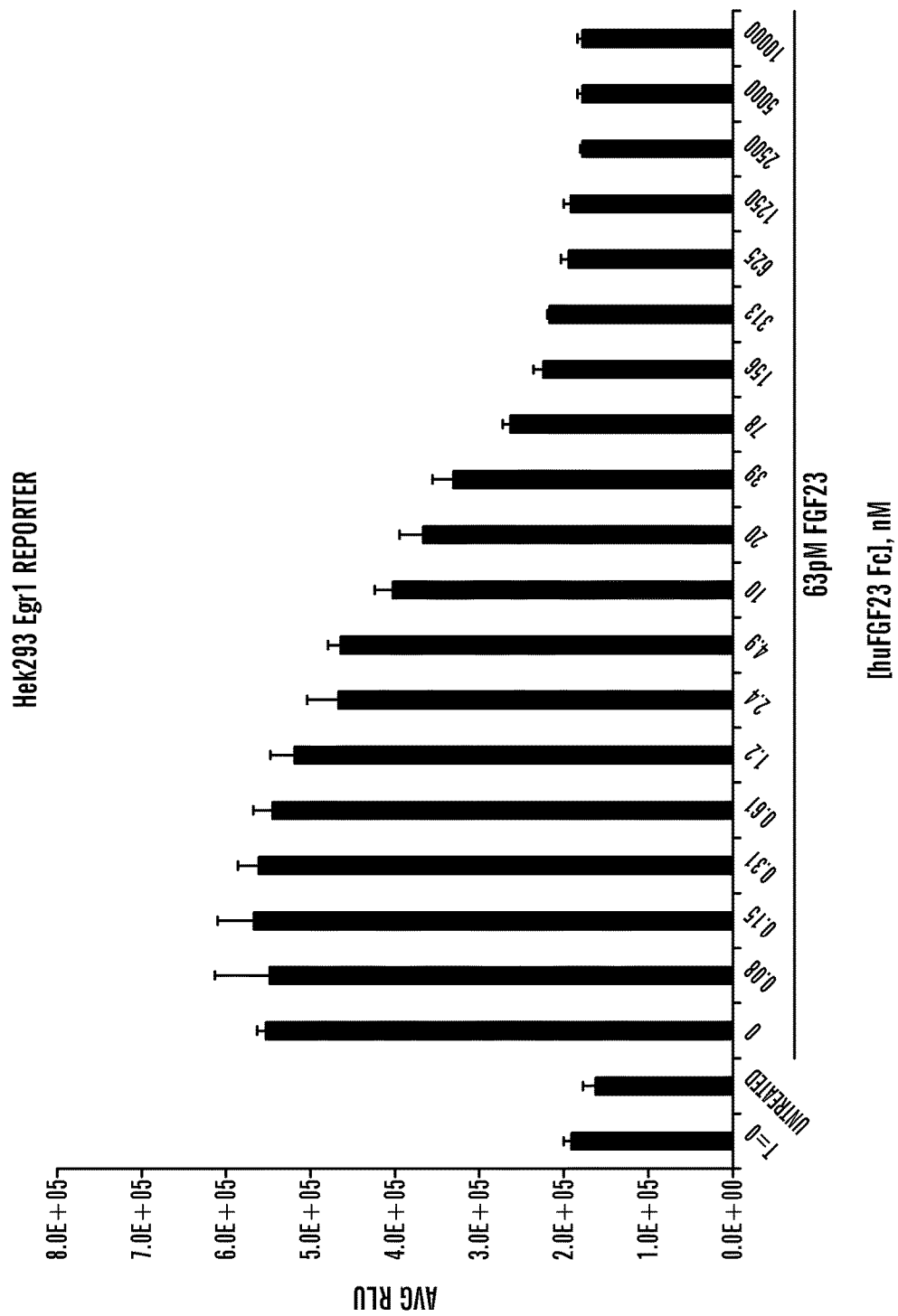
FIG. 6A shows dose-dependent inhibition by the FGF23 c-tail Fc of FGF23-mediated induction of Egr1-luciferase activity (after assay optimization).
Figure 6B:
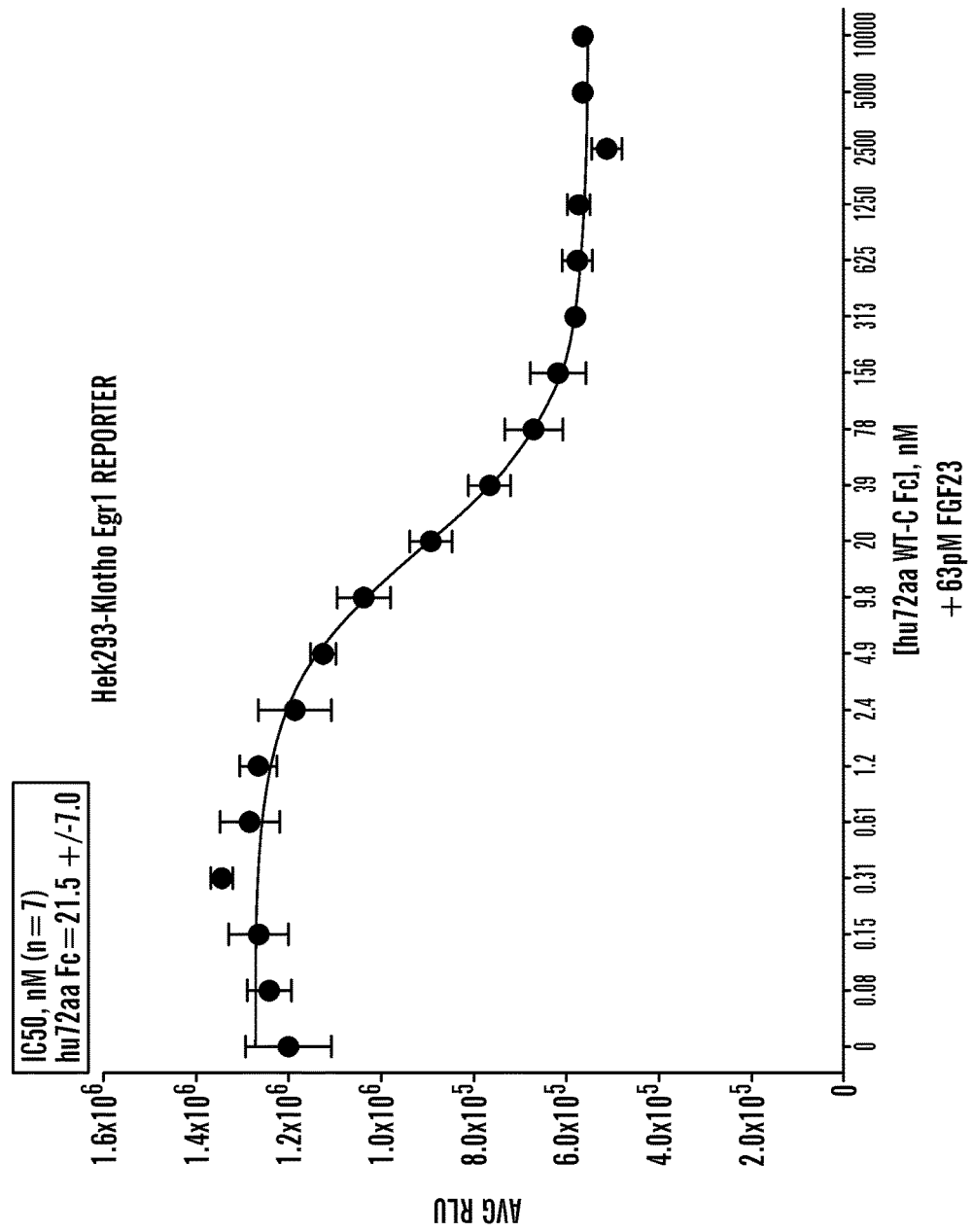
FIG. 6B shows the dose-inhibition response curve for FGF23 c-tail Fc and the IC50 values derived from the curve.
Figure 6C:
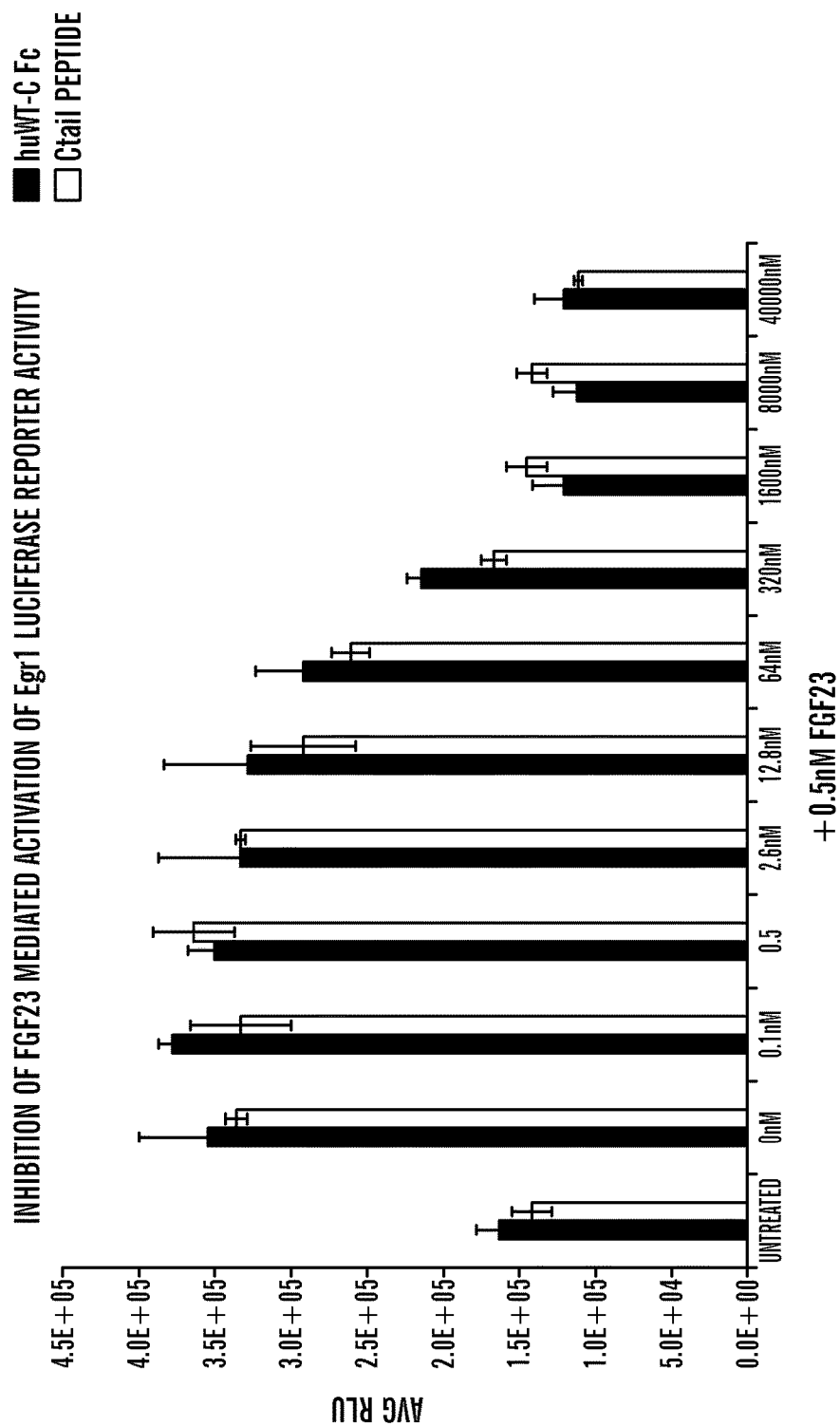
FIG. 6C shows dose-dependent inhibition by the FGF23 c-tail Fc or unconjugated FGF23 c-tail peptide of FGF23-mediated induction of Egr1-luciferase activity (prior to assay optimization).
Figure 6D:
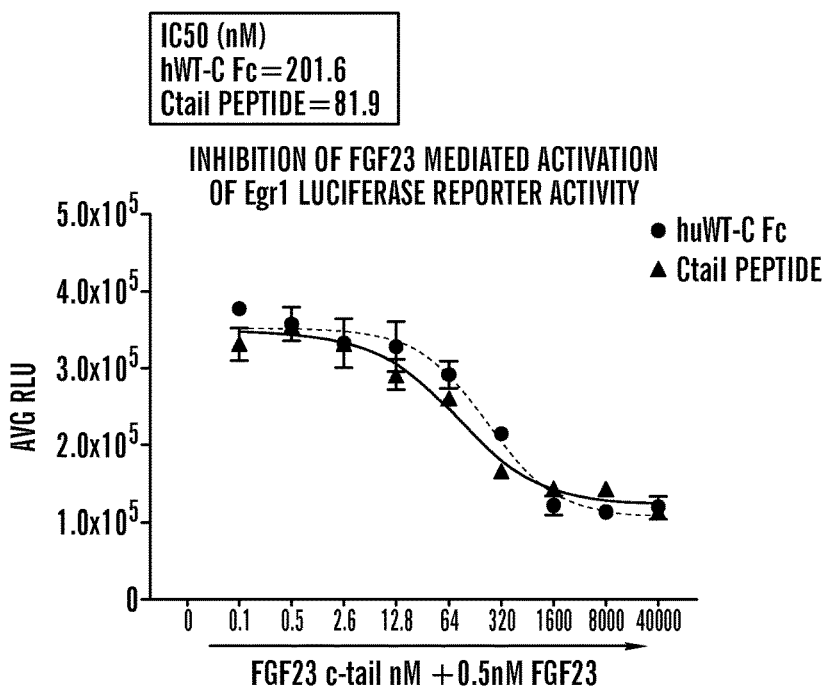
FIG. 6D shows the dose-inhibition response curves for FGF23 c-tail Fc and unconjugated FGF23 c-tail peptide and the IC50 values derived from these curves.

The ability of the FGF23 c-tail Fc fusion protein to inhibit FGF23-mediated induction of the transcription factor Egr1, a known downstream mediator of FGF signaling, was assessed in order to determine whether half-life extension engineering of the 72aa FGF23 c-tail peptide compromised the inhibitory potency of the peptide. HEK293 cells, engineered to stably express both α-klotho and an Egr1 luciferase reporter, were pre-treated with increasing amounts of FGF23 c-tail Fc prior to stimulating the cells with a sub-saturating amount of recombinant FGF23. The cells were then assessed in a luciferase reporter assay, and the results are shown in FIGS. 6A-6D. As shown in FIGS. 6C and 6D, the FGF23 c-tail Fc inhibits luciferase activity in a dose dependent manner, with an IC50 of 201.6 nM. By comparison, the unconjugated FGF23 c-tail peptide inhibited FGF23 signaling with an IC50 of 81.9 nM in this assay. As shown in the additional results provided in FIGS. 6A and 6B, the FGF23 c-tail Fc inhibits luciferase activity in a dose dependent manner, generating an IC50 of 21.5 nM (after assay optimization). The data show that the c-terminal fusion of the FGF23 c-tail to a human Fc molecule devoid of effector function does not substantially reduce the FGF23-inhibitory potency of the FGF23 c-tail peptide.

Figure 7:
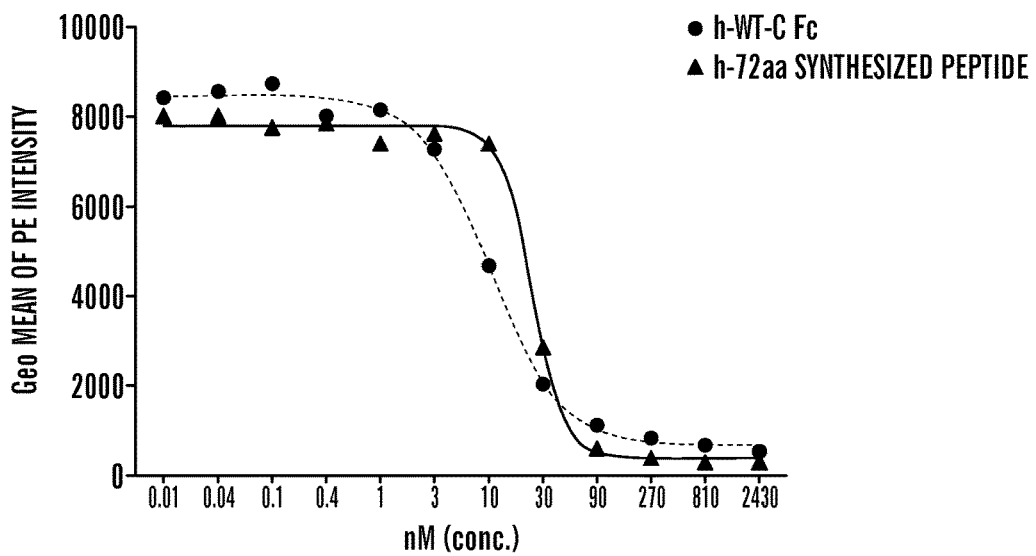
FIG. 7 depicts a graph illustrating dose-dependent inhibition by the FGF23 c-tail Fc or unconjugated FGF23 c-tail peptide of FGF23 binding to HEK293-aKlotho cells. Mean fluorescence intensity is plotted against the concentration of FGF23 binding competitor, namely the FGF23 c-tail Fc fusion or unconjugated FGF23 c-tail peptide.

In order to establish that competitive inhibition was happening at the level of receptor binding, cell-based binding competition experiments were performed using flow cytometry and HEK293 cells ectopically expressing αKlotho. As stated above, HEK293 cells endogenously express several FGFRs (Kurosu et al., (2006) J Biol Chem 281: 6120-6123; Yamazaki et al., (2010) J Cell Biochem 111:1210-1221), including cognate FGFRs of FGF23. Binding of a sub-saturating dose of FGF23 to HEK293-αklotho cells was assessed in the absence or presence of increasing amounts of the FGF23 c-tail Fc fusion or the unconjugated FGF23 c-tail peptide. Inhibition of FGF23 binding by either of the two competitors was quantitated by plotting the mean florescence (PE) intensity obtained at each concentration of binding competitor used in this assay. IC50 values were derived from the resulting inhibition binding curves (FIG. 7). The data show that the FGF23 c-tail Fc fusion molecule, like the unconjugated FGF23 c-tail peptide, inhibits FGF23 at the level of receptor binding.

Example 6: FGF23 C-Tail Fc Modulation of Serum Phosphorus and 1,25VitD

This example illustrates the effect of the Human FGF23 C-tail Fc on serum phosphorus and 1,25VitD in wild-type rats.

Figure 8A:
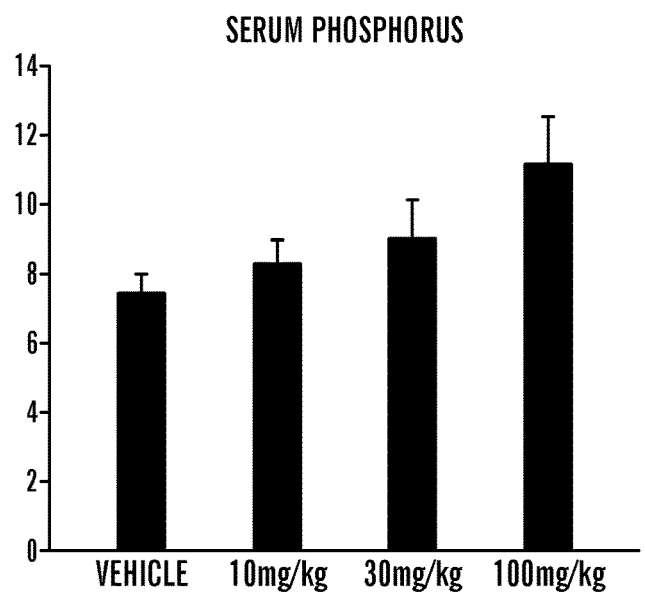
FIG. 8A shows mean serum concentrations of phosphate.
Figure 8B:
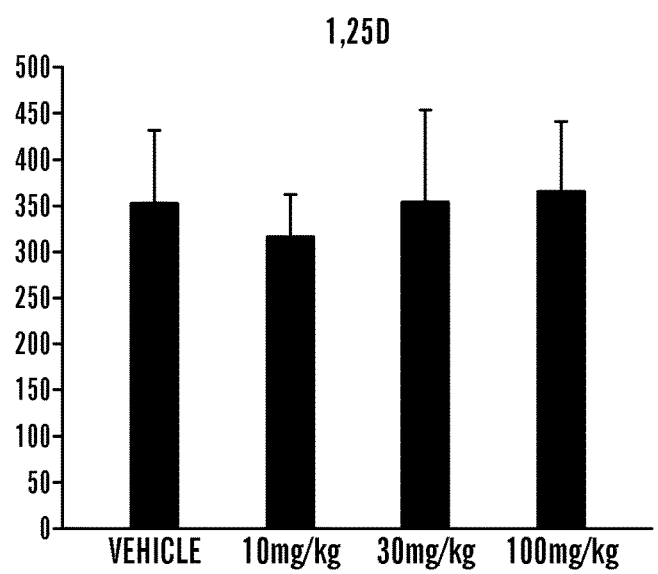
FIG. 8B shows mean serum concentrations of 1,25VitD.

FGF23 c-tail Fc was injected into healthy rats twice per week over 2 weeks at 10, 30 and 100 mg/kg. Both phosphorous and 1,25VitD levels in the serum on day 15, 24 hours post final dosing were measured. The FGF23 c-tail Fc treatment caused a dose-dependent increase in serum phosphorous compared to vehicle treatment (FIG. 8A). In contrast, and unexpectedly, serum 1,25 VitD levels did not change in response to the FGF23 c-tail Fc treatment, not even in response to the highest dose of FGF23 c-tail Fc used in these studies (FIG. 8B). These data provide evidence that the FGF23 c-tail Fc molecule causes modulation of the phosphate pathways in vivo without changing or leading to a change in serum 1,25VitD levels. Notably, 1,25VitD is a known potent inducer of FGF23 gene expression, and its increase under treatment with other FGF23 antagonists, such as FGF23 antibodies, sets in motion a vicious cycle of further FGF23 accumulation in disease conditions with already elevated FGF23 levels.

Example 7: Modulation of Phosphate Levels in Hyp Mice Via Regulation of NaPi2A Expression This example illustrates the therapeutic effect of Murine FGF23 C-tail Fc on phosphate levels in Hyp mice via regulation of NaPi2A expression.

Example 6 demonstrates that the FGF23 c-tail fusion proteins of the present invention can modulate the phosphate pathway in a wild-type setting. However, in order for the FGF23 c-tail to be used as a therapeutic in the treatment of XLH, the FGF23 c-tail fusion protein must be able to modulate phosphate levels in a manner robust enough to impact bone quality. A 7-week study using Hyp mice was completed to assess whether treatment with the FGF23 c-tail Fc could ameliorate hypophosphatemia and improve bone integrity in the absence of soft tissue mineralization. As in human disease, Hyp mice have elevated levels of FGF23 due to a mutation in the phosphate-regulating gene with homology to endopeptidases located on the X chromosome (PHEX), an endopeptidase expressed in the bone (Sitara, (2004) Matrix Biol. November:23(7):421-32; Liu, (2006) Am J Physiol Endocrinol Metab. 291(1):E38-49). For this study mice were injected twice per week subcutaneously between the ages of 5-12 weeks, including the active growth phase of the animals. Serum and urine chemistry, bone integrity and soft-tissue mineralization were assessed at the end of the study. Of note, though the human FGF23 c-tail fusion protein does crossreact in rodents, a surrogate molecule was used for this study in order to prevent immunogenicity over the length of the study which might compromise the data interpretation.

The surrogate molecule was shown to have similar potency to the human molecule in vitro when using an all murine system vs. an all human system respectively. The potency of the human and murine constructs were determined via both competitive inhibition using SPR and cellular viability assays (Cell Titer Glo). Specifically, for derivation of the Ki full-length FGF23 was bound to the Biacore Chip with a set amount of pre-formed receptor complex combined with increasing amounts of the FGF23 c-tail constructs floated over the chip. Experiments were done in a species specific manner meaning that all components were from a single species, either mouse or human. For the functional experiments, BAF3 cells were engineered to stably express FGFR1c and α-klotho. BAF3 cells are dependent on IL-3 for growth. However, upon expression of FGFR1c and α-klotho in the absence of IL-3 cell viability can be maintained upon addition of FGF23. Addition of the FGF23 c-tail Fc inhibits FGF23 in this context, in a dose dependent manner allowing calculation of an 1050. Once again this was done in a species specific manner. As Shown in Table 8, both the Ki and 1050s are comparable across species.

TABLE 8

Comparative Potency of Human and Murine
FGF23 c-tail Fusion Proteins

| Construct | IC50 | Ki |
|---|---|---|
| Human FGF23 c-tail Fc | 53 nM | 13 nM |
| Murine FGF23 c-tail Fc | 35 nM | 10 nM |

Figure 9A:
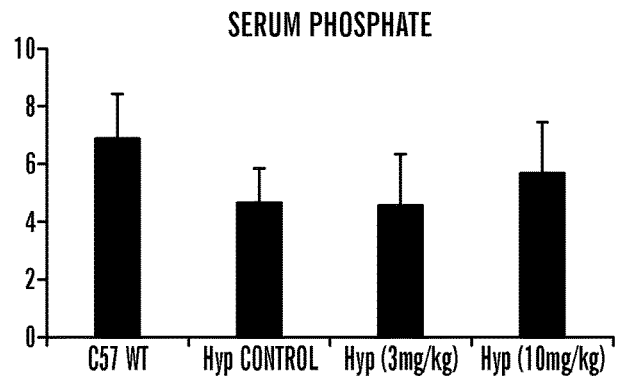
FIG. 9, comprising panels A, B, and C, depicts graphs showing serum concentrations and fractional renal excretion of phosphate, and renal NaPi2A mRNA expression in HYP mice following 7-weeks treatment with the murine FGF23 c-tail Fc fusion protein. Serum phosphate levels are shown in FIG. 9A. The Fractional Excretion of Phosphate (FEPHOSH (ratio of: (serum creatinine/serum phosphorus)/(urine creatinine/urine phosphorous))) is shown in FIG. 9B.
FIG. 9C shows NaPi2A expression relative to B2 microglobulin as measured by QPCR.
Figure 9B:
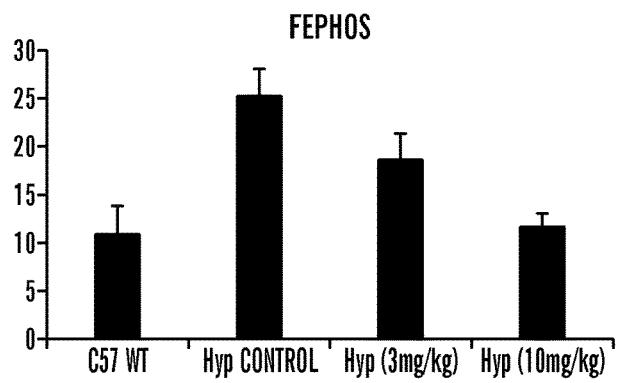

Consistent with Example 6, a trend in serum phosphate elevation was seen upon treatment, 24 hrs post dose at day 52 (FIG. 9A). Of note, serum phosphorous was only modulated at the highest dose and did not reach levels seen in wild-type animals at this timepoint. Phosphate excretion was dose responsive and normalization occurred in the 10 mg/kg treatment group (FIG. 9B). These data show that the FGF23 c-tail Fc impacts phosphate levels in a diseased setting and affects phosphate excretion to a greater extent than serum phosphorous at this time point.

Figure 9C:
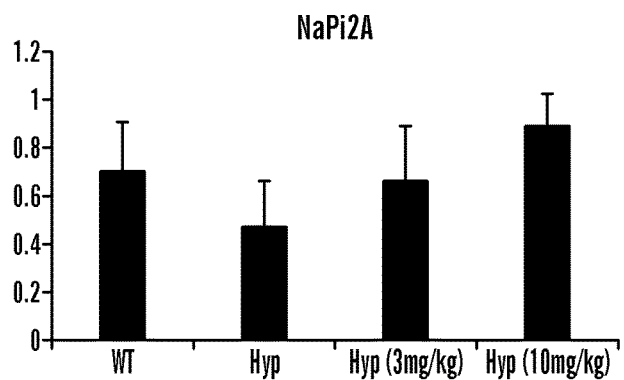

FGF23 modulates phosphate levels via downregulation of the sodium transporters located within the kidney; thus increasing phosphate excretion {Shimada, 2004; Gattineni, 2009}. In order to verify the mechanism of action by which the FGF23 c-tail Fc was modulating phosphate levels, NaPi2a expression was assessed relative to B2 microglobulin from total kidney RNA in animals at the end of the study using QPCR. As shown in FIG. 9C, a dose dependent increase in NaPi2a expression is found upon treatment with the FGF23 c-tail Fc. These results verify that the FGF23 c-tail Fc antagonizes FGF23 function at a known target in vivo, providing mechanistic evidence of appropriate target engagement.

Example 8: Modulation of Serum 1,25VitD and Calcium

This example illustrates the therapeutic effect of murine FGF23 C-Tail Fc on serum levels of 1,25VitD and calcium in Hyp mice.

Figure 10A:
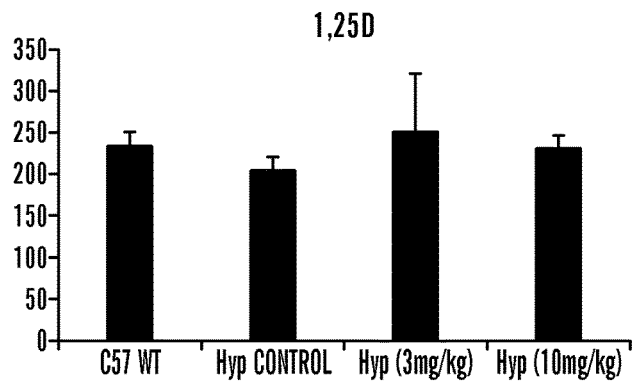
FIG. 10, comprising panels A, B, and C, depicts graphs showing serum concentrations of 1,25VitD and calcium, and fractional renal excretion of calcium in HYP mice following 7-weeks treatment with the murine FGF23 c-tail Fc fusion protein. Serum 1,25VitD levels are shown in FIG. 10A. Serum calcium levels are shown in FIG. 10B, and the Fractional Excretion of Calcium (FECA (ratio of: (serum creatinine/serum calcium)/(urine creatinine/urine calcium))) is shown in FIG. 10C.

1,25VitD levels are normally increased by hypophosphatemia via increased expression of 1α-hydroxylase (1αOH) in the kidney {Bergwitz, 2010}. This compensatory response is suppressed in settings of elevated circulating FGF23, which inhibits the formation of 1,25 VitD in the kidney by decreasing 1αOH expression. Thus in Hyp animals, which have persistently elevated serum FGF23, 1,25 VitD levels remain low—'inappropriately' low—in spite of hypophosphatemia. Inhibition of the FGF23 pathway using an anti-FGF23 antibody cocktail or small molecule inhibitors to the FGFRs or MAPK pathway in Hyp mice result in a strong increase in 1,25 VitD levels post dosing (Aono, (2009) J Bone Miner Res. 2009 November; 24(11):1879-88; Wohrle et al (2013) J Bone Miner Res. 28(4):899-911; Zhang et al, (2012) Endocrinology. 153(4):1806-16). By contrast and unexpectedly, serum 1,25 VitD levels did not change in Hyp mice treated for 7 weeks with the FGF23 c-tail Fc, not even with the highest treatment dose used in these studies (FIG. 10A). The 1,25 VitD levels were measured at the same 24 hr time point post treatment as in the studies on the other FGF23 inhibitors. This data is consistent with the lack of a change in serum 1,25 VitD seen in response to treatment of healthy animals with FGF23 c-tail Fc (Example 6), and differentiates the FGF23 c-tail Fc from other inhibitors of the FGF23 pathway, which all lead to an increase in serum 1,25 VitD.

Figure 10B:
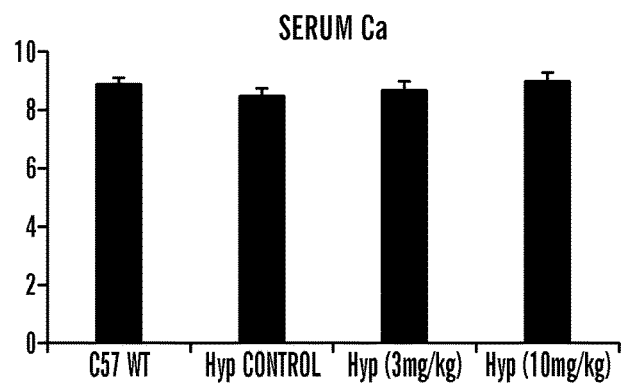
Figure 10C:
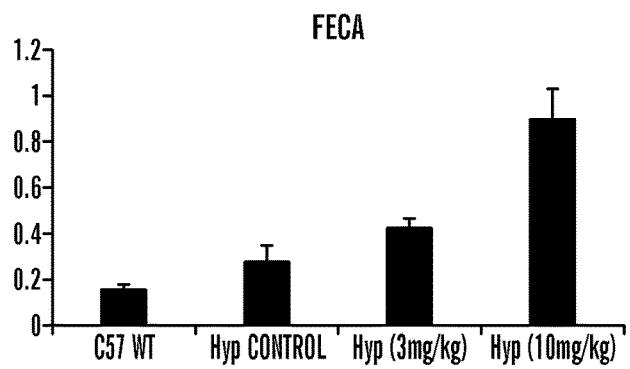
Figure 11A:
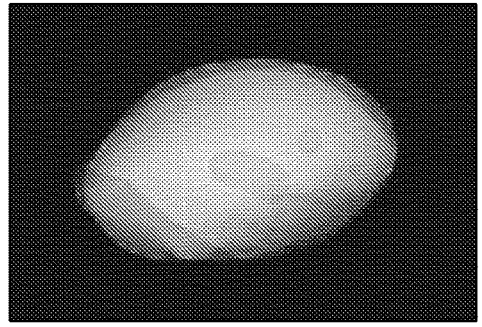
FIG. 11A represents the wild-type control mouse.
Figure 11B:
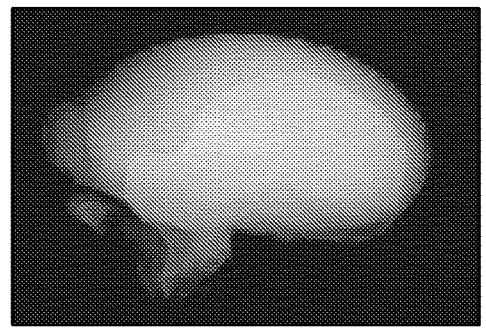
FIG. 11B depicts the HYP control mouse.
Figure 11C:
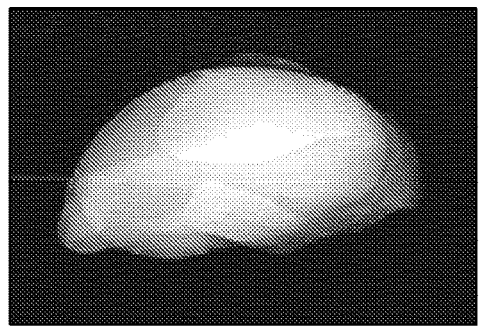
FIG. 11C shows the Hyp mouse treated with 3 mg/kg of murine FGF23 c-tail Fc.
Figure 11D:
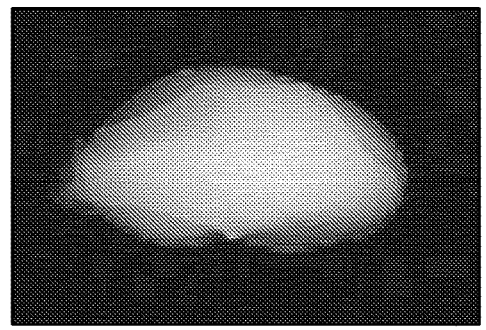
FIG. 11D shows the Hyp mouse treated with 10 mg/kg murine FGF23 c-tail Fc.

Serum calcium levels and renal calcium excretion were also measured in Hyp mice after 7 weeks treatment with the FGF23 c-tail Fc. As shown in FIGS. 10B and 10C, serum calcium remained within the normal range in spite of increased renal calcium excretion. While the increase in calcium excretion likely reflects antagonism by the FGF23$^{C\text{-}tail}$-Fc fusion molecule of the renal calcium-conserving action of FGF23 (Andrukhova et al., EMBO (2014) 33: pp. 229-246), the mechanisms that offset the renal calcium loss and maintain normocalcemia remain to be elucidated. Importantly, treatment of Hyp mice with other FGF23 antagonists, namely anti-FGF23 antibodies, results in hypercalcemia (Aono, 2009), which, together with increased serum phosphate levels (relative to untreated Hyp mice), poses a risk for soft tissue mineralization, and hence a safety risk. The FGF23 c-tail Fc molecule may bear less risk in this respect because it does not lead to hypercalcemia. Consistent with this, no soft tissue mineralization was observed in mice after chronic treatment with the FGF23 c-tail Fc, not even with the highest treatment dose (see Example 9 below).

Example 9: Absence of Renal Tissue Mineralization

An example is provided for the lack of soft tissue mineralization in Hyp mice chronically treated with muFGF23 c-tail Fc.

Faxitron X-ray was used to assess kidney calcification in treated and non-treated Hyp animals relative to wild-type controls across a 7 week study. Three groups of Hyp mice were dosed with phosphate buffered saline, 3 mg/kg of muFGF23 c-tail Fc and 10 mg/kg of muFGF23 c-tail Fc respectively. Wild-type mice were dosed with phosphate buffer. Following scheduled necropsy on Day 16 and 52, the left kidney was x-rayed using a MX-20 Digital radiography system (Faxitron X-ray LLC, Wheeling Ill.). There was no visible calcification in the kidneys of mice enrolled in the study regardless of strain and/or dosing regimen deployed (FIGS. 11 A-D).

Example 10: Improved Cancellous Bone and Bone Mineral Content and Bone Histology This example illustrates the effect of the FGF23 C-tail Fc fusion protein on cancellous bone and bone mineral content.

Phosphate plays a major role in the mineralization of osteoid and cartilage matrix at the growth plate. In hypophosphatemic conditions such as XLH, the bone matrix is compromised (Carpenter, 2011). Several radiologic techniques were used to assess the bone quality of the treated and non-treated Hyp animals relative to wild-type controls across a 7 week study.

Figure 12A:
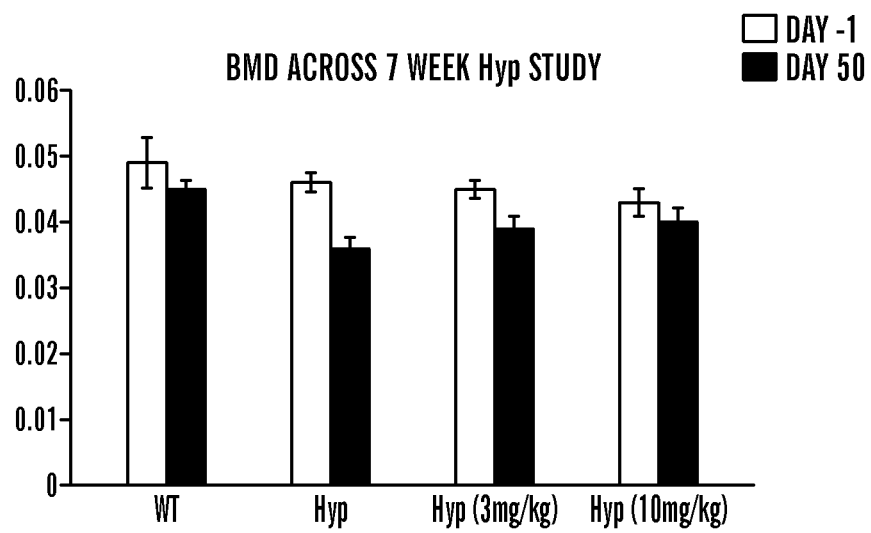
FIG. 12, comprising panels A and B, shows graphs illustrating the bone mineral density and bone mineral content of Hyp mice treated with 3 mg/kg or 10 mg/kg muFGF23 c-tail Fc relative to age-match control Hyp and wild-type mice following dosing for a total of 7 weeks. Bone mineral density is shown in FIG. 12A as assessed by PIXIMUS. Bone mineral content is shown in FIG. 12B.
Figure 12B:
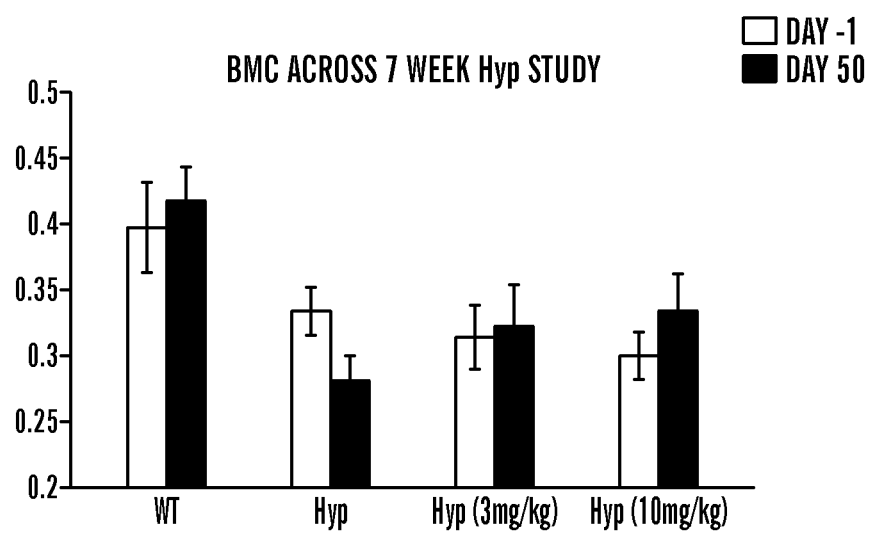

PIXIMus is an automated densitometer used to measure Bone Mineral Density/Content in live animals, thereby allowing quantitative assessment of bone parameters. Consistent with published data (Eicher, (1976) Proc Natl Acad Sci USA. 73(12):4667-71; Meyer, (1980) Adv Exp Med Biol.128:351-9), relative to age matched wild-type mice, Hyp mice display several skeletal abnormalities including: significantly lower bone mineral content (BMC) and bone mineral density (BMD) and smaller bone volume despite having somewhat larger bones. Together these parameters are a strong indication of poor bone mineralization that eventually leads to compromised bone strength. Over the course of the study, treatment with 3 mg/kg of muFGF23 c-tail Fc showed a trend of improved BMC and BMD, while treatment with 10 mg/kg of muFGF23 c-tail Fc produced significant improvement (Table 9). Importantly, individual animals within a group behaved similarly (FIGS. 12A and 12B). These data are consistent with increased modulation of clinical chemistries in the 10 mg/kg treated animals and provide evidence for improved bone mineralization.

TABLE 9

| Bone Parameters on D50 | | | | |
|---|---|---|---|---|
| | C57 WT | Hyp Control untreated | Hyp 3 mg/kg | Hyp 10 mg/kg |
| BMD (gm/cm$^2$) | 0.045 ± 0.001 | 0.036 ± 0.002 | 0.039* ± 0.002 | 0.04* ± 0.002 |
| BMC (gm) | 0.042 ± 0.026 | 0.028 ± 0.009 | 0.032* ± 0.031 | 0.033* ± 0.028 |

*p < 0.01

Figure 13A:
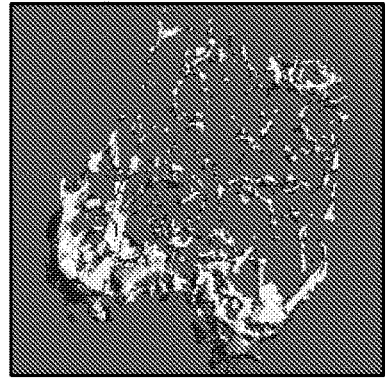
FIG. 13A represents the wild-type control mouse.
Figure 13B:
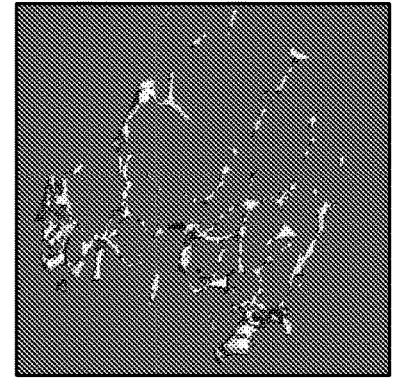
FIG. 13B depicts the HYP mouse.
Figure 13C:
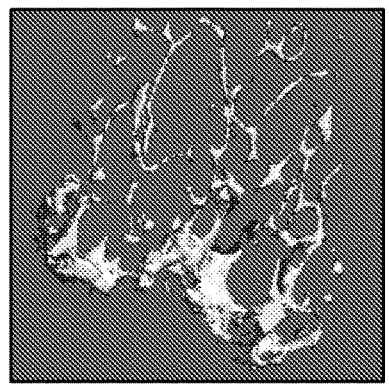
FIG. 13C shows the Hyp mouse treated with 3 mg/kg of muFGF23 c-tail Fc.
Figure 13D:
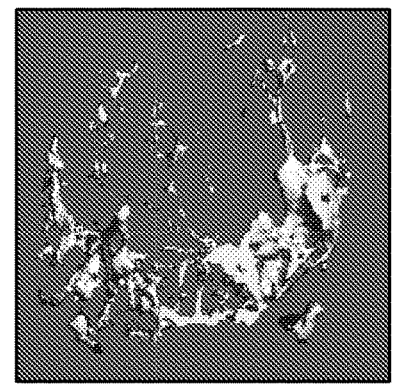
FIG. 13D shows the Hyp mouse treated with 10 mg/kg muFGF23 c-tail Fc.

To more directly assess bone quality cancellous bone of the distal femoral metaphysis was imaged by performing ex vivo microCT. Cancellous bone is highly vascularized and metabolic, and is therefore suitable for assessing remodeling. FIG. 13A represents the wild-type mouse. FIG. 13B depicts the Hyp mouse. FIG. 13C shows the Hyp mouse treated with 3 mg/kg of muFGF23 c-tail Fc. FIG. 13D shows the Hyp mouse treated with 10 mg/kg muFGF23 c-tail Fc. As expected, the wild-type control mice had far more cancellous bone at the distal femoral metaphysis than the Hyp control animals did. Remarkably, a clear dose responsive increase was seen upon treatment. As bone is typically laid down at the bone shafts, the increase in cancellous bone is most evident at the bone edge where ossification occurs.

Figure 14A:
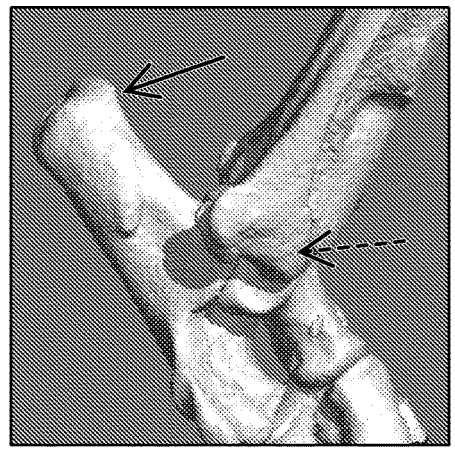
FIG. 14A represents the wild-type control mouse.
Figure 14B:
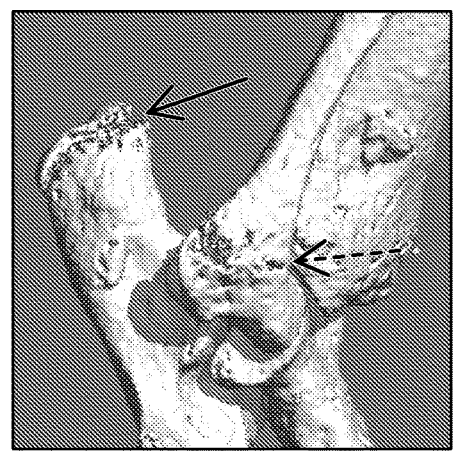
FIG. 14B depicts the HYP mouse.
Figure 14C:
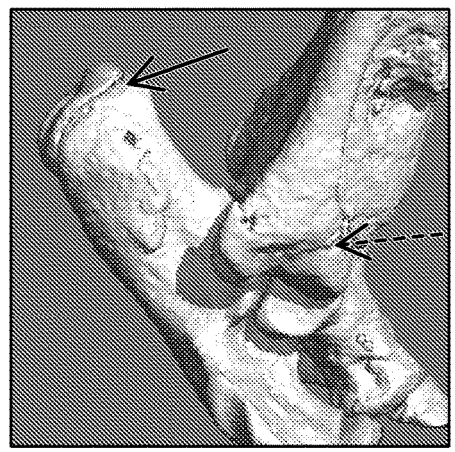
FIG. 14C shows the Hyp mouse treated with 3 mg/kg of muFGF23 c-tail Fc.
Figure 14D:
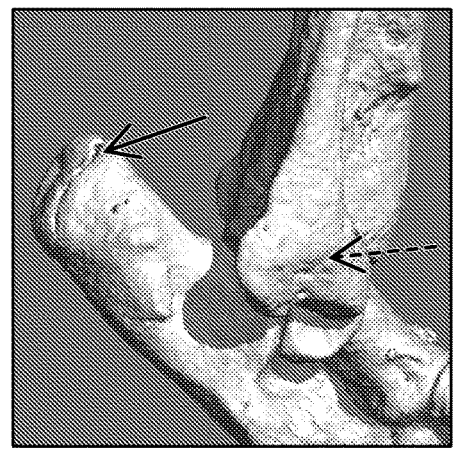
FIG. 14D shows the Hyp mouse treated with 10 mg/kg muFGF23 c-tail Fc.

The poor bone quality of Hyp control animals can also be evidenced by the large areas of scalloped bone surfaces, numerous lacunae and open growth plates seen throughout the entire hock joint as visualized by three-dimensional microCT (FIG. 14B). By day 50 of the study, growth plates closed in the wild-type animals but remained open in the Hyp controls (FIGS. 14A and 14B). Animals treated with 10 mg/kg of the muFGF23 c-tail Fc fusion showed a restoration of bone surfaces and significantly diminished pathological lacunae over the time of the study (FIG. 14D). In addition, closure of epiphyseal growth plates occurred upon treatment with 10 mg/kg of the muFGF23 c-tail Fc fusion (FIG. 14D). Consistent with other data, animals in the 3 mg/kg group showed moderate improvement; although the growth plates remained open in these animals (FIG. 14C).

Figure 15A:
FIG. 15A represents the wild-type control mouse.
Figure 15B:
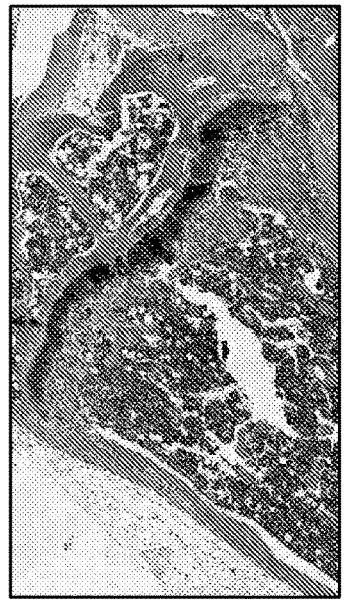
FIG. 15B depicts the HYP mouse.
Figure 15C:
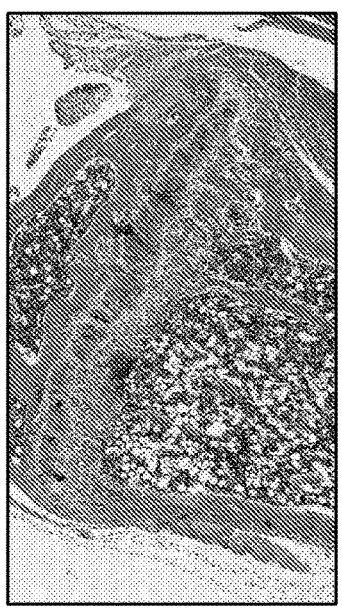
FIG. 15C shows the Hyp mouse treated with 3 mg/kg of muFGF23 c-tail Fc.
Figure 15D:
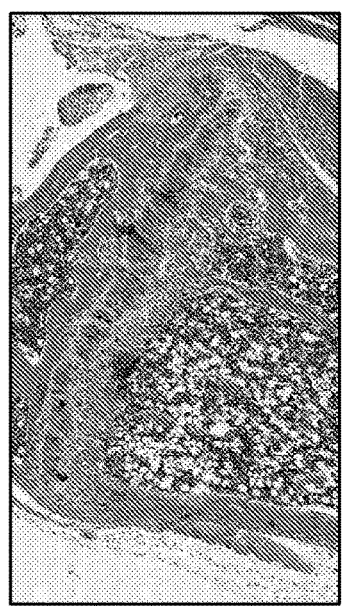
FIG. 15D shows the Hyp mouse treated with 10 mg/kg muFGF23 c-tail Fc.

Histological analysis of bone architecture at the tibial physes was also assessed. The physis is the part of the bone responsible for bone lengthening, constituting an area that separates the metaphysis and the epiphysis, in which long bone growth occurs. FIG. 15A represents the wild-type mouse. FIG. 15B depicts the Hyp mouse. FIG. 15C shows the Hyp mouse treated with 3 mg/kg of muFGF23 c-tail Fc. FIG. 15D shows the Hyp mouse treated with 10 mg/kg muFGF23 c-tail Fc. As seen in FIGS. 15A-D, Hyp control animals had a large area of cartilage and poorly mineralized bone. In contrast, the wild-type mice had a thin layer of cartilage followed by a zone of ossification. Strikingly, there is marked improvement of the structure in both treatment groups, with cartilage being replaced in a dose dependent manner by mineralized bone.

Together these data demonstrate that the FGF23 c-tail Fc fusion protein is able to mediate significant bone improvement in Hyp animals over 7 weeks.

Example 11: Half-Life Extension of the FGF23 c-tail Peptide

This example illustrates the increased serum half-life of the FGF23 C-tail Fc fusion protein of the present invention.

Figure 16A:
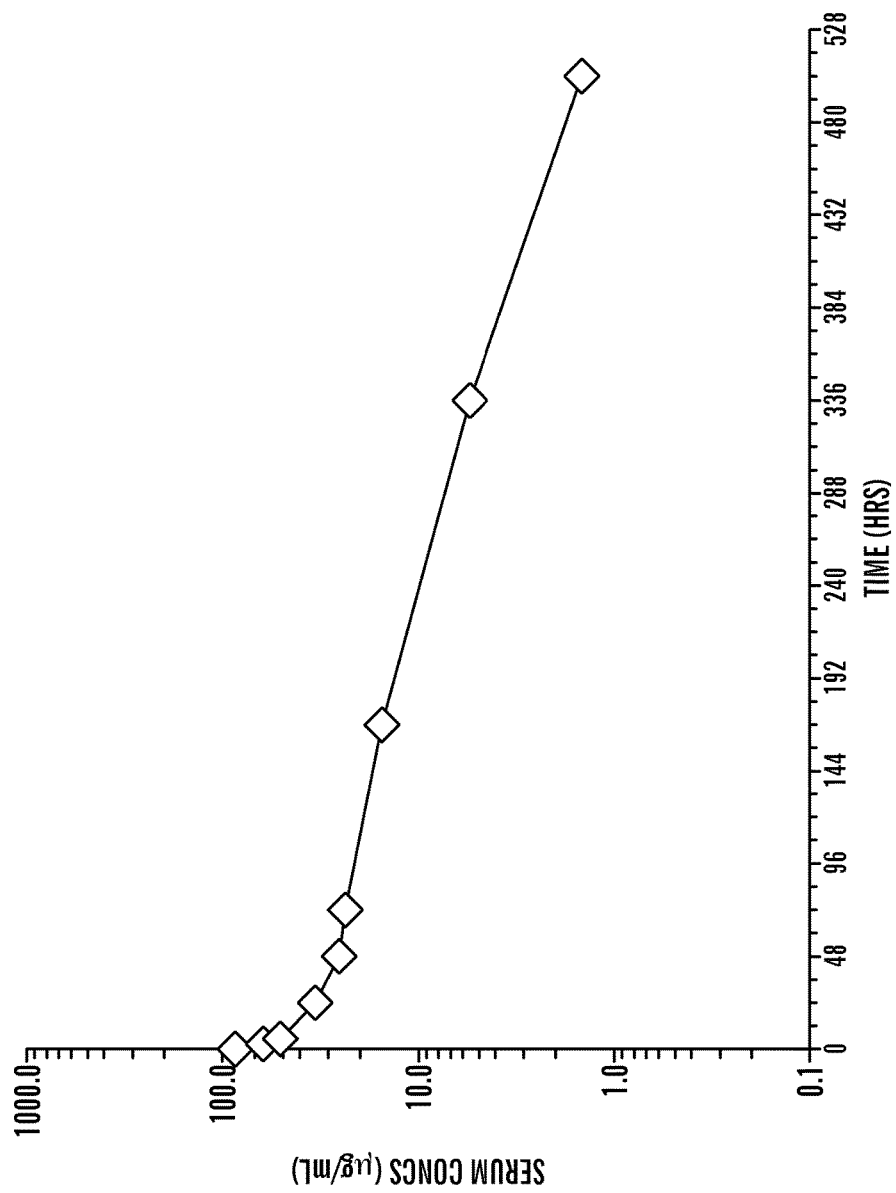
FIG. 16A shows the mean serum concentration following IV administration of huFGF23 c-tail Fc in male Cynomolgus monkeys treated with 3 mg/kg of huFGF23 c-tail Fc.
Figure 16B:
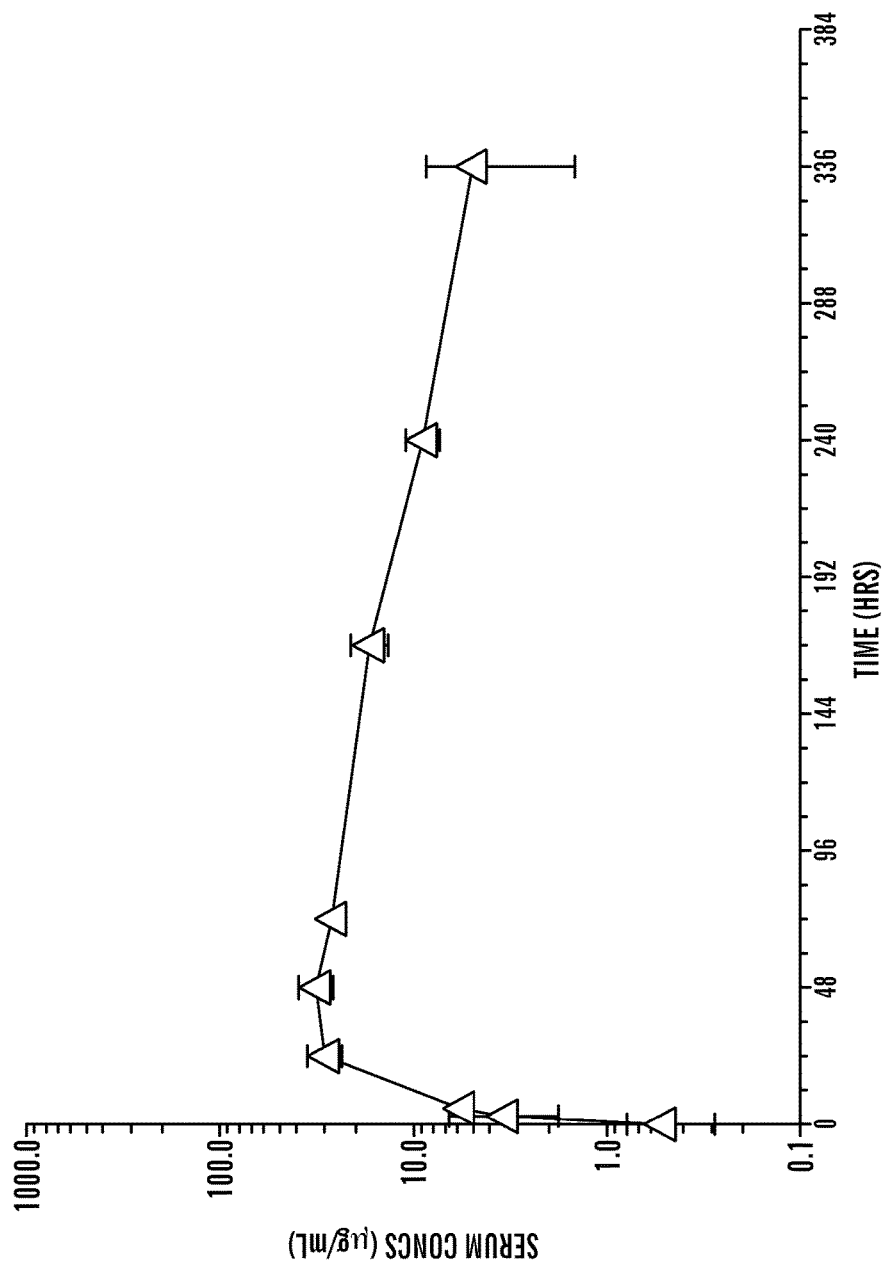
FIG. 16B shows the mean serum concentration following subcutaneous administration of huFGF23 c-tail Fc in male Sprague Dawley rats treated with 10 mg/kg of huFGF23 c-tail Fc.

The human wild type 72 amino acid FGF23 c-tail peptide without post-translational modifications (SEQ ID NO: 2, FGF23$^{180-251}$) has an estimated short half-life in Sprague-Dawley rats (Goetz et al, PNAS 107, p 407 2010). The half-life of this peptide, and a peptide with post-translational modifications, in monkeys and humans is unknown at this time. See, Khosravi et al, *J Clin Endocrinol & Metabol* (2007) 92: 2374-2377. To determine the circulation half-life of the FGF23 c-tail Fc and confirm that the conjugation of the FGF23 c-tail peptide to an Fc molecule extends the half-life of the peptide, a single injection of HuFGF23 c-tail Fc (SEQ ID NO: 15) was given to Sprague-Dawley rats as well as Cynomolgus monkeys, and plasma concentrations of the fusion molecule were measured at a series of time points post injection (FIGS. 16A and 16B). Plasma samples were analyzed using an ELISA method consisting of commercially available reagents (Abcam). The half-life of the huFGF23-Fc in monkeys was 84.5 hrs after an IV dose of 3 mg/kg, and the half-life in rats was 104 hrs after an SC dose of 10 mg/kg.

Example 12: Binding Properties of the Fc-FGF23 Fusion Protein

To date, the binding affinity of the FGF23 c-tail peptide across the cognate receptor complexes of FGF23 and the nature of the binding itself have not been well defined. In the absence of this information, it was difficult to predict whether fusion to an Fc molecule would affect the intrinsic binding properties of the FGF23 c-tail peptide and whether any potential changes would be consistent across the various FGFR/αklotho receptor complexes. In order to approach these questions, BAF3 cells (a murine pro-B cell line that does not express endogenous FGFRs or Klotho) were engineered to express distinct receptor complexes and the binding of recombinant human FGF23 across these cell lines was assessed. As noted above, FGF23 protein (both human and mouse described herein) were produced using a Mouse myeloma cell line (NSO). Subsequently, the ability of either the FGF23 c-tail peptide or the FGF23 c-tail Fc to competitively inhibit FGF23 binding was assessed. The first, preliminary results from these experiments are shown in FIGS. 17A-17B.

Figure 17A:
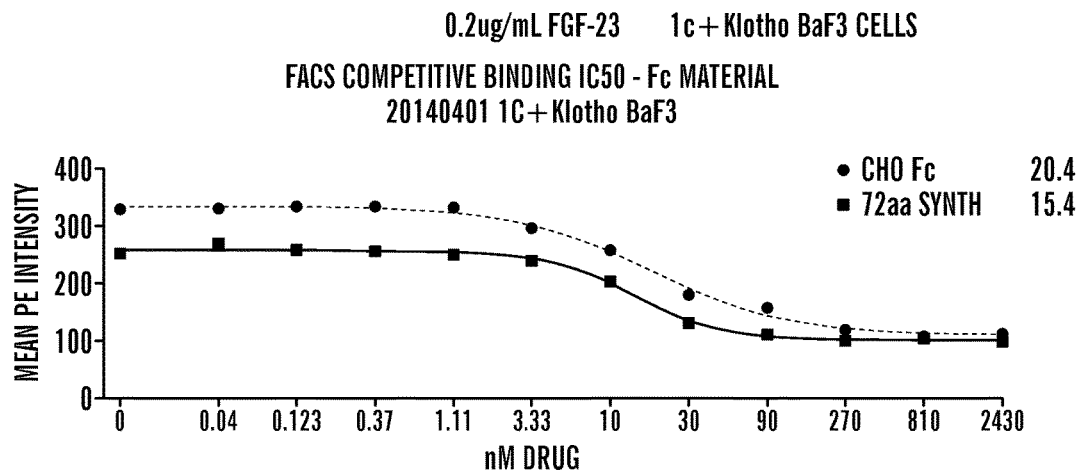
FIG. 17A shows dose-dependent inhibition by the FGF23 c-tail peptide and the FGF23 c-tail Fc, respectively, of FGF23 binding to BaF3 cells expressing FGFR1c and αklotho.
Figure 17B:
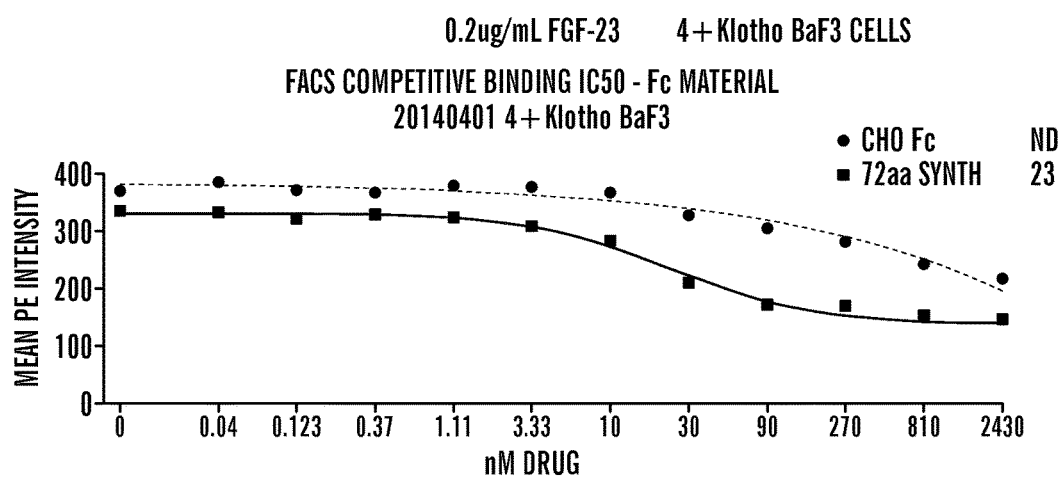
FIG. 17B shows dose-dependent inhibition by the FGF23 c-tail peptide and the FGF23 c-tail Fc, respectively, of FGF23 binding to BaF3 cells expressing FGFR4 and αklotho. Note that the FGF23 c-tail Fc is less potent than the unconjugated FGF23 c-tail peptide at inhibiting FGF23 binding to BaF3-FGFR4/αklotho cells.

The FGF23 c-tail peptide and the FGF23 c-tail Fc had a similar ability to compete with FGF23 binding on BAF3 lines engineered to express FGFR1c/αklotho (FIG. 17A). In contrast, the FGF23 c-tail Fc appeared to be less potent than the unconjugated FGF23 c-tail peptide at inhibiting FGF23 binding to BAF3 cells engineered to express FGFR[4]/αklotho (FIG. 17B). These data imply a change in the intrinsic binding properties of the FGF23 c-tail peptide, specifically on the FGFR4/αklotho complex, evoked by the conjugation of the peptide to an Fc molecule. Although proof for such a change awaits the determination of crystal structures of binary/ternary complexes of FGFR, αKlotho, and FGF23, it was certainly not predictable.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A fusion protein comprising a fibroblast growth factor 23 c-tail (FGF23 c-tail) protein fused to a heterologous amino acid sequence, wherein the FGF23 c-tail protein comprises an amino acid sequence corresponding to the sequence beginning at residue 1 and ending at any one of residues 67 to 72 of SEQ ID NO:2, wherein the heterologous amino acid sequence comprises a human IgG1 Fc domain, and wherein said fusion protein modulates serum phosphate levels but does not substantially modulate serum 1,25-dihydroxycholecalciferol (1,25 VitD) levels.

2. The fusion protein of claim 1, wherein the FGF23 c-tail protein comprises the sequence shown in SEQ ID NO:2, SEQ ID NO:3, SEQ ID NO: 4, SEQ ID NO:5, SEQ ID NO:6 or SEQ ID NO:7.

3. The fusion protein of claim 1, wherein the FGF23 c-tail protein comprises the sequence shown in SEQ ID NO:2.

4. The fusion protein of claim 1, wherein the FGF23 c-tail protein is fused to the heterologous amino acid sequence via a linker.

5. The fusion protein of claim 4, wherein the linker is a peptidyl linker comprising a sequence selected from:

```
                                         (SEQ ID NO: 10)
   a. GSGEGEGSEGSG;

(SEQ ID NO: 11)
   b. GGSEGEGSEGGS;
   and (SEQ ID NO: 12)
   c. GGGGS.
```

6. The fusion protein of claim 1, wherein the Fc domain comprises the amino acid sequence of residues 1-231 shown in SEQ ID NO:13 or residues 1-231 shown in SEQ ID NO:14.

7. The fusion protein of claim 1 comprising an amino acid sequence selected from the group consisting of the sequence shown in SEQ ID NO:15, SEQ ID NO:16, SEQ ID NO:17, SEQ ID NO:18, SEQ ID NO:19, and SEQ ID NO:20.

8. The fusion protein of claim 7 comprising the amino acid sequence shown in SEQ ID NO:15.

9. A pharmaceutical composition comprising the fusion protein of claim 1 and a pharmaceutically acceptable agent.

10. A method of increasing serum phosphate levels in a patient in need thereof, the method comprising administering to the patient the fusion protein of claim 1.

11. The method of claim 10, wherein the patient has renal phosphate wasting disorder.

12. The method of claim 10, wherein the patient has a disease or disorder selected from the group consisting of autosomal dominant hypophosphatemic rickets (ADHR), X-linked hypophosphatemic rickets (XLH), tumor-induced osteomalacia (TIO), fibrous dysplasia (FD), and chronic kidney disease (CKD).

13. The method of claim 10, wherein the patient has left ventricular hypertrophy or hyperparathyroidism.

14. An FGF23 c-tail Fc fusion protein comprising an amino acid sequence consisting of the amino acid sequence shown in SEQ ID NO:15.

\* \* \* \* \*